United States Patent
Kent et al.

(10) Patent No.: US 12,121,566 B2
(45) Date of Patent: Oct. 22, 2024

(54) METHODS FOR TREATING GOUT

(71) Applicant: Horizon Therapeutics USA, Inc., Deerfield, IL (US)

(72) Inventors: Jeffrey D. Kent, Deerfield, IL (US); Brian Lamoreaux, Lake Forest, IL (US)

(73) Assignee: Horizon Therapeutics USA, Inc., Deerfield, IL (US)

( * ) Notice: Subject to any disclaimer, the term of this patent is extended or adjusted under 35 U.S.C. 154(b) by 348 days.

(21) Appl. No.: 16/777,625

(22) Filed: Jan. 30, 2020

(65) Prior Publication Data

US 2020/0237879 A1 Jul. 30, 2020

Related U.S. Application Data

(60) Provisional application No. 62/903,562, filed on Sep. 20, 2019, provisional application No. 62/798,782, filed on Jan. 30, 2019.

(51) Int. Cl.
| | | |
|---|---|---|
| A61K 38/44 | (2006.01) | |
| A61K 9/00 | (2006.01) | |
| A61K 31/52 | (2006.01) | |
| A61P 19/06 | (2006.01) | |

(52) U.S. Cl.
CPC ............ *A61K 38/44* (2013.01); *A61K 9/0053* (2013.01); *A61K 31/52* (2013.01); *A61P 19/06* (2018.01)

(58) Field of Classification Search
CPC ...... A61K 38/44; A61K 9/0053; A61K 31/52; A61K 9/0019; A61P 19/06
See application file for complete search history.

(56) References Cited

U.S. PATENT DOCUMENTS

| | | |
|---|---|---|
| 1,141,973 A | 6/1915 | Nichols |
| 3,023,259 A | 2/1962 | Coler et al. |
| 3,148,322 A | 9/1964 | Booe et al. |
| 3,451,996 A | 6/1969 | Sumyk et al. |
| 3,613,231 A | 10/1971 | Pugh et al. |
| 3,616,231 A | 10/1971 | Bergmeyer et al. |
| 3,715,697 A | 2/1973 | Them |
| 3,918,995 A | 11/1975 | Palmer et al. |
| 3,931,399 A | 1/1976 | Bohn et al. |
| 4,027,676 A | 6/1977 | Mattei |
| 4,064,010 A | 12/1977 | Harris et al. |
| 4,141,973 A | 2/1979 | Balazs |
| 4,169,764 A | 10/1979 | Takezawa et al. |
| 4,179,337 A | 12/1979 | Davis et al. |
| 4,251,431 A | 2/1981 | Carswell et al. |
| 4,297,344 A | 10/1981 | Schwinn et al. |
| 4,301,153 A | 11/1981 | Rosenberg |
| 4,312,979 A | 1/1982 | Takemoto et al. |
| 4,315,852 A | 2/1982 | Leibowitz et al. |
| 4,317,878 A | 3/1982 | Nakanishi et al. |
| 4,343,735 A | 8/1982 | Menge et al. |
| 4,343,736 A | 8/1982 | Uemura et al. |
| 4,376,110 A | 3/1983 | David et al. |
| 4,421,650 A | 12/1983 | Nagasawa et al. |
| 4,425,431 A | 1/1984 | Takemoto et al. |
| 4,445,745 A | 5/1984 | Cartesse |
| 4,450,103 A | 5/1984 | Konrad et al. |
| 4,460,575 A | 7/1984 | D'Hinterland et al. |
| 4,460,683 A | 7/1984 | Gloger et al. |
| 4,485,176 A | 11/1984 | Bollin, Jr. et al. |
| 4,753,796 A | 6/1988 | Moreno et al. |
| 4,766,106 A | 8/1988 | Katre et al. |
| 4,797,474 A | 1/1989 | Patroni et al. |
| 4,816,567 A | 3/1989 | Cabilly et al. |
| 4,847,079 A | 7/1989 | Kwan |
| 4,847,325 A | 7/1989 | Shadle et al. |
| 4,917,888 A | 4/1990 | Katre et al. |
| 4,945,086 A | 7/1990 | Benitz et al. |
| 4,946,778 A | 8/1990 | Ladner et al. |
| 4,966,963 A | 10/1990 | Patroni |
| 4,987,076 A | 1/1991 | Takashio et al. |
| 4,992,339 A | 2/1991 | Georgopoulos |
| 4,992,531 A | 2/1991 | Patroni et al. |
| 5,008,377 A | 4/1991 | Patroni et al. |
| 5,010,183 A | 4/1991 | Macfarlane |

(Continued)

FOREIGN PATENT DOCUMENTS

| | | |
|---|---|---|
| CN | 1218578 A | 6/1999 |
| CN | 1268254 A | 9/2000 |

(Continued)

OTHER PUBLICATIONS

Hershfield M. et al. Induced and Pre-Existing Anti-PEG Antibody in a Trial of Every 3 Week Dosing of Pegloticase for Refractory Gout . . . Arthritis Research and Therapy 16(2)1-11, Mar. 2014. (Year: 2014).*
Wuthrich H. et al. Guidelines for the Treatment of Gout: A Swiss Perspective Swiss Medical Weekly 146:1-7 2016. (Year: 2016).*
Milgroom A. et al. Immunosuppressant Use and Gout in the Prevalent Solid Organ Transplant Population. J of the American Society of Nephrology 29:152 Abstract TH-P0160, 2018. (Year: 2018).*
Tutton R. Pharmacogenomic Biomarkers in Drug Labels Pharmacogenetics 15(3)297-304, 2014 (Year: 2014).*
Berhanu A. et al. Pegloticase Failure and a Possible Solution. Seminars in Arthritis and Rheumatism 46(6)754-758, 2017. (Year: 2017).*
Brigham M. et al. Immunosuppressant Use and Gout in the Prevalent Solid Organ Transplantation Population. J of the American Society of Nephrology 230(2)103-110 2020. (Year: 2020).*
Assadi F. Managing New Onset Gout in Pediatric Renal Transplant Recipients. J of Nephrology 26(4)624-628 2013. (Year: 2013).*

(Continued)

*Primary Examiner* — Aaron J Kosar
(74) *Attorney, Agent, or Firm* — David Roadcap

(57) ABSTRACT

The disclosure provides methods of treating gout in patients comprising administering a PEGylated uricase. Also provided are methods of treating gout in patients comprising co-administering a PEGylated uricase and azathioprine immunosuppressive therapy. Also provided are methods of reducing intolerance or enhancing immuno-tolerance to a PEGylated uricase and prolonging the urate lowering effect comprising co-administration of the PEGylated uricase and azathioprine immunosuppressive therapy.

16 Claims, 1 Drawing Sheet

(56) References Cited

U.S. PATENT DOCUMENTS

| | | |
|---|---|---|
| 5,114,916 A | 5/1992 | Shirahata et al. |
| 5,122,614 A | 6/1992 | Zalipsky |
| 5,225,539 A | 7/1993 | Winter |
| 5,283,317 A | 2/1994 | Saifer et al. |
| 5,286,637 A | 2/1994 | Veronese et al. |
| 5,362,641 A | 11/1994 | Fuks et al. |
| 5,382,518 A | 1/1995 | Caput et al. |
| 5,428,128 A | 6/1995 | Mensi-Fattohi et al. |
| 5,458,135 A | 10/1995 | Patton et al. |
| 5,468,478 A | 11/1995 | Saifer et al. |
| 5,529,915 A | 6/1996 | Phillips et al. |
| 5,541,098 A | 7/1996 | Caput et al. |
| 5,567,422 A | 10/1996 | Greenwald |
| 5,585,089 A | 12/1996 | Queen et al. |
| 5,612,460 A | 3/1997 | Zalipsky |
| 5,624,903 A | 4/1997 | Muller et al. |
| 5,633,227 A | 5/1997 | Muller et al. |
| 5,637,749 A | 6/1997 | Greenwald |
| 5,643,575 A | 7/1997 | Martinez et al. |
| 5,653,974 A | 8/1997 | Hung et al. |
| 5,711,944 A | 1/1998 | Gilbert et al. |
| 5,762,923 A | 6/1998 | Gross et al. |
| 5,766,897 A | 6/1998 | Braxton |
| 5,776,627 A | 7/1998 | Mao et al. |
| 5,811,096 A | 9/1998 | Aleman et al. |
| 5,816,397 A | 10/1998 | Pratt |
| 5,824,784 A | 10/1998 | Kinstler et al. |
| 5,879,832 A | 3/1999 | Vu et al. |
| 5,880,255 A | 3/1999 | Delgado et al. |
| 5,919,455 A | 7/1999 | Greenwald et al. |
| 5,929,231 A | 7/1999 | Malkki et al. |
| 5,932,462 A | 8/1999 | Harris et al. |
| 5,948,668 A | 9/1999 | Hartman et al. |
| 5,955,336 A | 9/1999 | Shigyo et al. |
| 5,998,051 A | 12/1999 | Poirier et al. |
| 6,006,753 A | 12/1999 | Efendic |
| 6,130,318 A | 10/2000 | Wild et al. |
| 6,168,880 B1 | 1/2001 | Snyder et al. |
| 6,201,110 B1 | 3/2001 | Olsen et al. |
| 6,204,635 B1 | 3/2001 | Sullivan |
| 6,211,341 B1 | 4/2001 | Zeelon et al. |
| 6,245,901 B1 | 6/2001 | Von et al. |
| 6,468,210 B2 | 10/2002 | Iliff |
| 6,475,143 B2 | 11/2002 | Iliff |
| 6,524,241 B2 | 2/2003 | Iliff |
| 6,527,713 B2 | 3/2003 | Iliff |
| 6,544,679 B1 | 4/2003 | Petillo et al. |
| 6,562,517 B1 | 5/2003 | Misra et al. |
| 6,569,093 B2 | 5/2003 | Iliff |
| 6,575,235 B2 | 6/2003 | Zupanick et al. |
| 6,576,235 B1 | 6/2003 | Williams et al. |
| 6,608,892 B2 | 8/2003 | Shaffer et al. |
| 6,783,965 B1 | 8/2004 | Sherman et al. |
| 6,897,206 B2 | 5/2005 | Sackeyfio et al. |
| 6,913,915 B2 | 7/2005 | Ensor et al. |
| 7,056,713 B1 | 6/2006 | Hershfield et al. |
| 7,723,089 B2 | 5/2010 | Williams et al. |
| 7,811,800 B2 | 10/2010 | Hartman et al. |
| 7,927,589 B2 | 4/2011 | Williams et al. |
| 7,927,852 B2 | 4/2011 | Sherman et al. |
| 7,952,330 B2 | 5/2011 | Mori |
| 7,964,381 B2 | 6/2011 | Hartman et al. |
| 8,034,594 B2 | 10/2011 | Hartman et al. |
| 8,067,553 B2 | 11/2011 | Williams et al. |
| 8,148,123 B2 | 4/2012 | Hartman et al. |
| 8,178,334 B2 | 5/2012 | Hartman et al. |
| 8,188,224 B2 | 5/2012 | Hartman et al. |
| 8,293,228 B2 | 10/2012 | Hartman et al. |
| 8,465,735 B2 | 6/2013 | Hartman et al. |
| 8,541,205 B2 | 9/2013 | Hartman et al. |
| 8,618,267 B2 | 12/2013 | Williams et al. |
| 8,722,226 B2 | 5/2014 | Chiang et al. |
| 8,722,227 B2 | 5/2014 | Chiang et al. |
| 8,749,341 B2 | 6/2014 | Takeda |
| 8,778,552 B2 | 7/2014 | Chiang et al. |
| 8,913,915 B2 | 12/2014 | Makino |
| 8,921,064 B2 | 12/2014 | Sherman et al. |
| 8,993,159 B2 | 3/2015 | Chiang et al. |
| 9,017,980 B2 | 4/2015 | Hartman et al. |
| 9,153,833 B2 | 10/2015 | Chiang et al. |
| 9,178,200 B2 | 11/2015 | Bazzarella et al. |
| 9,184,464 B2 | 11/2015 | Chiang et al. |
| 9,203,092 B2 | 12/2015 | Slocum et al. |
| 9,293,781 B2 | 3/2016 | Chiang et al. |
| 9,362,583 B2 | 6/2016 | Chiang et al. |
| 9,377,454 B2 | 6/2016 | Rosario-Jansen et al. |
| 9,385,392 B2 | 7/2016 | Chiang et al. |
| 9,401,501 B2 | 7/2016 | Bazzarella et al. |
| 9,402,827 B2 | 8/2016 | Miner et al. |
| 9,437,864 B2 | 9/2016 | Tan et al. |
| 9,484,569 B2 | 11/2016 | Doherty et al. |
| 9,534,013 B2 | 1/2017 | Fischer et al. |
| 9,583,780 B2 | 2/2017 | Chiang et al. |
| 9,614,231 B2 | 4/2017 | Carter et al. |
| 9,670,467 B2 | 6/2017 | Hartman et al. |
| 9,786,944 B2 | 10/2017 | Chiang et al. |
| 9,812,674 B2 | 11/2017 | Bazzarella et al. |
| 9,825,280 B2 | 11/2017 | Chiang et al. |
| 9,831,518 B2 | 11/2017 | Chiang et al. |
| 9,831,519 B2 | 11/2017 | Chiang et al. |
| 9,831,522 B2 | 11/2017 | Tan et al. |
| 9,885,024 B2 | 2/2018 | Williams et al. |
| 9,926,537 B2 | 3/2018 | Hartman et al. |
| 9,926,538 B2 | 3/2018 | Hartman et al. |
| 10,115,970 B2 | 10/2018 | Ota et al. |
| 10,122,044 B2 | 11/2018 | Tan et al. |
| 10,139,399 B2 | 11/2018 | Rosario-Jansen et al. |
| 10,153,651 B2 | 12/2018 | Taylor et al. |
| 10,160,958 B2 | 12/2018 | Hartman et al. |
| 10,181,587 B2 | 1/2019 | Ota et al. |
| 10,230,128 B2 | 3/2019 | Chiang et al. |
| 10,236,518 B2 | 3/2019 | Chiang et al. |
| 10,236,537 B2 | 3/2019 | Hamaguchi et al. |
| 10,411,310 B2 | 9/2019 | Chiang et al. |
| 10,483,582 B2 | 11/2019 | Chiang et al. |
| 10,497,935 B2 | 12/2019 | Ota et al. |
| 10,522,870 B2 | 12/2019 | Tan et al. |
| 10,566,581 B2 | 2/2020 | Bazzarella et al. |
| 10,566,603 B2 | 2/2020 | Slocum et al. |
| 10,593,952 B2 | 3/2020 | Ota et al. |
| 10,601,239 B2 | 3/2020 | Taylor et al. |
| 10,637,038 B2 | 4/2020 | Zagars et al. |
| 10,665,836 B2 | 5/2020 | Cho et al. |
| 10,731,139 B2 | 8/2020 | Hartman et al. |
| 10,734,672 B2 | 8/2020 | Chen et al. |
| 10,777,852 B2 | 9/2020 | Woodford et al. |
| 10,823,727 B2 * | 11/2020 | Rosario-Jansen ...... A61K 47/60 |
| 10,854,869 B2 | 12/2020 | Bazzarella et al. |
| 10,886,521 B2 | 1/2021 | Zagars et al. |
| 10,910,858 B2 | 2/2021 | Taylor et al. |
| 10,957,940 B2 | 3/2021 | Tan et al. |
| 10,964,973 B2 | 3/2021 | Tan et al. |
| 11,005,087 B2 | 5/2021 | Ota et al. |
| 11,018,365 B2 | 5/2021 | Chiang et al. |
| 11,024,903 B2 | 6/2021 | Ota et al. |
| 11,094,487 B2 | 8/2021 | Lawrence et al. |
| 11,094,976 B2 | 8/2021 | Chiang et al. |
| 11,121,437 B2 | 9/2021 | Bazzarella et al. |
| 11,139,467 B2 | 10/2021 | Zagars et al. |
| 11,145,909 B2 | 10/2021 | Chiang et al. |
| 11,309,531 B2 | 4/2022 | Slocum et al. |
| 11,342,567 B2 | 5/2022 | Chiang et al. |
| 11,345,899 B2 | 5/2022 | Hartman et al. |
| 11,394,049 B2 | 7/2022 | Tan et al. |
| 11,594,793 B2 | 2/2023 | Bazzarella et al. |
| 11,598,767 B2 | 3/2023 | Rosario-Jansen et al. |
| 11,611,061 B2 | 3/2023 | Zagars et al. |
| 11,639,927 B2 | 5/2023 | Rosario-Jansen et al. |
| 11,781,119 B2 | 10/2023 | Hartman et al. |
| 2001/0038938 A1 | 11/2001 | Takahashi et al. |
| 2002/0010319 A1 | 1/2002 | Ansaldi et al. |
| 2002/0151703 A1 | 10/2002 | Yokoyama et al. |
| 2003/0082786 A1 | 5/2003 | Ensor et al. |
| 2003/0166249 A1 | 9/2003 | Williams et al. |

(56) References Cited

U.S. PATENT DOCUMENTS

| | | |
|---|---|---|
| 2004/0028995 A1 | 2/2004 | Shelekhin et al. |
| 2004/0081890 A1 | 4/2004 | Xing et al. |
| 2005/0014240 A1 | 1/2005 | Sherman et al. |
| 2005/0084478 A1 | 4/2005 | Liu et al. |
| 2006/0188971 A1 | 8/2006 | Hershfield et al. |
| 2007/0274977 A1 | 11/2007 | Hartman et al. |
| 2008/0031864 A1 | 2/2008 | Williams et al. |
| 2008/0057048 A1 | 3/2008 | Sherman et al. |
| 2008/0145876 A1 | 6/2008 | Armstrong et al. |
| 2008/0159976 A1 | 7/2008 | Hartman et al. |
| 2008/0254355 A1 | 10/2008 | Muraoka et al. |
| 2009/0023715 A1 | 1/2009 | Brown et al. |
| 2009/0169534 A1 | 7/2009 | Hartman et al. |
| 2009/0209021 A1 | 8/2009 | Hartman et al. |
| 2009/0286139 A1 | 11/2009 | Awano |
| 2009/0315666 A1 | 12/2009 | Ueda et al. |
| 2009/0317889 A1 | 12/2009 | Fischer et al. |
| 2010/0021821 A1 | 1/2010 | Kim et al. |
| 2010/0047671 A1 | 2/2010 | Chiang et al. |
| 2010/0152305 A1 | 6/2010 | Cedarbaum |
| 2010/0160351 A1 | 6/2010 | Jenkins et al. |
| 2010/0255351 A1 | 10/2010 | Ijaz et al. |
| 2010/0323264 A1 | 12/2010 | Chiang et al. |
| 2010/0323422 A1 | 12/2010 | Williams et al. |
| 2010/0323423 A1 | 12/2010 | Williams et al. |
| 2011/0104751 A1 | 5/2011 | Hartman et al. |
| 2011/0189520 A1 | 8/2011 | Carter et al. |
| 2011/0200848 A1 | 8/2011 | Chiang et al. |
| 2011/0217755 A1 | 9/2011 | Hartman et al. |
| 2011/0274948 A1 | 11/2011 | Duduta et al. |
| 2011/0287466 A1 | 11/2011 | Sherman et al. |
| 2012/0070876 A1 | 3/2012 | Hartman et al. |
| 2012/0121936 A1 | 5/2012 | Baek et al. |
| 2012/0149083 A1 | 6/2012 | Williams et al. |
| 2012/0164499 A1 | 6/2012 | Chiang et al. |
| 2012/0225046 A1 | 9/2012 | Hartman et al. |
| 2012/0301454 A1 | 11/2012 | Rosario-Jansen et al. |
| 2012/0309085 A1 | 12/2012 | Hartman et al. |
| 2013/0052677 A1 | 2/2013 | Williams et al. |
| 2013/0055559 A1 | 3/2013 | Slocum et al. |
| 2013/0065122 A1 | 3/2013 | Chiang et al. |
| 2013/0084273 A1 | 4/2013 | Hartman et al. |
| 2013/0309547 A1 | 11/2013 | Bazzarella et al. |
| 2013/0330803 A1 | 12/2013 | Hartman et al. |
| 2013/0337319 A1 | 12/2013 | Doherty et al. |
| 2014/0004437 A1 | 1/2014 | Slocum et al. |
| 2014/0011060 A1 | 1/2014 | Yang et al. |
| 2014/0030623 A1 | 1/2014 | Chiang et al. |
| 2014/0039710 A1 | 2/2014 | Carter et al. |
| 2014/0154546 A1 | 6/2014 | Carter et al. |
| 2014/0170450 A1 | 6/2014 | Takahashi et al. |
| 2014/0170524 A1 | 6/2014 | Chiang et al. |
| 2014/0248521 A1 | 9/2014 | Chiang et al. |
| 2014/0315097 A1 | 10/2014 | Tan et al. |
| 2014/0363414 A1 | 12/2014 | Sherman et al. |
| 2015/0024279 A1 | 1/2015 | Tan et al. |
| 2015/0129081 A1 | 5/2015 | Chiang et al. |
| 2015/0140371 A1 | 5/2015 | Slocum |
| 2015/0140410 A1 | 5/2015 | Kim et al. |
| 2015/0171406 A1 | 6/2015 | Bazzarella et al. |
| 2015/0180033 A1 | 6/2015 | Oyama et al. |
| 2015/0197732 A1 | 7/2015 | Hartman et al. |
| 2015/0280185 A1 | 10/2015 | Lampe-Onnerud et al. |
| 2015/0280202 A1 | 10/2015 | Lee et al. |
| 2015/0280267 A1 | 10/2015 | Chiang et al. |
| 2015/0295272 A1 | 10/2015 | Chiang et al. |
| 2015/0357626 A1 | 12/2015 | Holman et al. |
| 2016/0013507 A1 | 1/2016 | Chiang et al. |
| 2016/0020042 A1 | 1/2016 | Stanton et al. |
| 2016/0035091 A1 | 2/2016 | Kubassova |
| 2016/0056490 A1 | 2/2016 | Chiang et al. |
| 2016/0056491 A1 | 2/2016 | Chiang et al. |
| 2016/0105042 A1 | 4/2016 | Taylor et al. |
| 2016/0126543 A1 | 5/2016 | Ota et al. |
| 2016/0133916 A1 | 5/2016 | Zagars et al. |
| 2016/0141593 A1 | 5/2016 | Min et al. |
| 2016/0158318 A1 | 6/2016 | Cohen et al. |
| 2016/0160188 A1 | 6/2016 | Williams et al. |
| 2016/0190544 A1 | 6/2016 | Slocum et al. |
| 2016/0211502 A1 | 7/2016 | Choi et al. |
| 2016/0218375 A1 | 7/2016 | Chiang et al. |
| 2016/0240896 A1 | 8/2016 | Zhang et al. |
| 2016/0268621 A1 | 9/2016 | Chiang et al. |
| 2016/0308218 A1 | 10/2016 | Ota et al. |
| 2016/0315301 A1 | 10/2016 | Kim et al. |
| 2016/0344006 A1 | 11/2016 | Ota et al. |
| 2016/0372802 A1 | 12/2016 | Chiang et al. |
| 2016/0377604 A1 | 12/2016 | Rosario-Jansen et al. |
| 2017/0018798 A1 | 1/2017 | Tan et al. |
| 2017/0025646 A1 | 1/2017 | Ota et al. |
| 2017/0025674 A1 | 1/2017 | Tan et al. |
| 2017/0033389 A1 | 2/2017 | Chiang et al. |
| 2017/0033390 A1 | 2/2017 | Chiang et al. |
| 2017/0077464 A1 | 3/2017 | Bazzarella et al. |
| 2017/0162863 A1 | 6/2017 | Doherty et al. |
| 2017/0166873 A1 | 6/2017 | Fischer et al. |
| 2017/0214034 A1 | 7/2017 | Ota et al. |
| 2017/0237111 A1 | 8/2017 | Holman et al. |
| 2017/0237112 A1 | 8/2017 | Holman et al. |
| 2017/0258927 A1 | 9/2017 | Johnston |
| 2017/0279108 A1 | 9/2017 | Herle |
| 2017/0288281 A1 | 10/2017 | Chiang et al. |
| 2017/0298326 A1 | 10/2017 | Hartman et al. |
| 2017/0313993 A1 | 11/2017 | Hartman et al. |
| 2017/0313994 A1 | 11/2017 | Hartman et al. |
| 2017/0313995 A1 | 11/2017 | Hartman et al. |
| 2017/0321193 A1 | 11/2017 | Hartman et al. |
| 2018/0008665 A1 | 1/2018 | Qiao et al. |
| 2018/0034090 A1 | 2/2018 | Chiang et al. |
| 2018/0102521 A1 | 4/2018 | Cho et al. |
| 2018/0127432 A1 | 5/2018 | Trzupek et al. |
| 2018/0175428 A1 | 6/2018 | Chiang et al. |
| 2018/0175445 A1 | 6/2018 | Tan et al. |
| 2018/0188242 A1 | 7/2018 | Rosario-Jansen et al. |
| 2018/0223263 A1 | 8/2018 | Sherman et al. |
| 2018/0233708 A1 | 8/2018 | Bazzarella et al. |
| 2018/0233722 A1 | 8/2018 | Holman et al. |
| 2018/0287220 A1 | 10/2018 | Woodford et al. |
| 2018/0289776 A1 | 10/2018 | Johnston |
| 2019/0036101 A1 | 1/2019 | Tyler et al. |
| 2019/0058184 A1 | 2/2019 | Bazzarella et al. |
| 2019/0245242 A1 | 8/2019 | Tan et al. |
| 2019/0316097 A1 | 10/2019 | Hartman et al. |
| 2019/0317083 A1 | 10/2019 | Rosario-Jansen et al. |
| 2019/0319460 A1 | 10/2019 | Taylor et al. |
| 2019/0326562 A1 | 10/2019 | Ota et al. |
| 2019/0348705 A1 | 11/2019 | Chen et al. |
| 2019/0355998 A1 | 11/2019 | Chiang et al. |
| 2019/0363351 A1 | 11/2019 | Ota et al. |
| 2019/0393477 A1 | 12/2019 | Lawrence et al. |
| 2020/0014025 A1 | 1/2020 | Zagars et al. |
| 2020/0044296 A1 | 2/2020 | Chiang et al. |
| 2020/0056160 A1 | 2/2020 | Fischer et al. |
| 2020/0106094 A1 | 4/2020 | Ota et al. |
| 2020/0161688 A1 | 5/2020 | Chiang et al. |
| 2020/0220118 A1 | 7/2020 | Bazzarella et al. |
| 2020/0220204 A1 | 7/2020 | Tan et al. |
| 2020/0237880 A1* | 7/2020 | Kent ..................... A61K 47/60 |
| 2020/0237881 A1* | 7/2020 | Kent ..................... A61K 31/519 |
| 2020/0259338 A1 | 8/2020 | Taylor et al. |
| 2020/0321597 A1 | 10/2020 | Zagars et al. |
| 2020/0321601 A1 | 10/2020 | Slocum et al. |
| 2020/0353057 A1 | 11/2020 | Kent et al. |
| 2020/0358129 A1 | 11/2020 | Chen et al. |
| 2020/0411825 A1 | 12/2020 | Bazzarella et al. |
| 2021/0079362 A1 | 3/2021 | Hartman et al. |
| 2021/0091366 A1 | 3/2021 | Bazzarella et al. |
| 2021/0167351 A1 | 6/2021 | Zagars et al. |
| 2021/0181187 A1 | 6/2021 | Rosario-Jansen et al. |
| 2021/0202935 A1 | 7/2021 | Wang et al. |
| 2021/0226192 A1 | 7/2021 | Aranami et al. |
| 2021/0249678 A1 | 8/2021 | Chiang et al. |
| 2021/0249695 A1 | 8/2021 | Aranami et al. |
| 2021/0265631 A1 | 8/2021 | Chen et al. |

(56) References Cited

U.S. PATENT DOCUMENTS

| | | |
|---|---|---|
| 2021/0359527 A1 | 11/2021 | Taylor et al. |
| 2021/0376380 A1 | 12/2021 | Tan et al. |
| 2021/0384516 A1 | 12/2021 | Lawrence et al. |
| 2022/0021019 A1 | 1/2022 | Tan et al. |
| 2022/0037749 A1 | 2/2022 | Bazzarella et al. |
| 2022/0052403 A1 | 2/2022 | Chen et al. |
| 2022/0077445 A1 | 3/2022 | Ota et al. |
| 2022/0085440 A1 | 3/2022 | Ota et al. |
| 2022/0093929 A1 | 3/2022 | Chen et al. |
| 2022/0115710 A1 | 4/2022 | Zagars et al. |
| 2022/0172916 A1 | 6/2022 | Lawrence et al. |
| 2022/0173446 A1 | 6/2022 | Chiang et al. |
| 2022/0200306 A1 | 6/2022 | Kusachi et al. |
| 2022/0231274 A1 | 7/2022 | Zagars et al. |
| 2022/0238923 A1 | 7/2022 | Chen et al. |
| 2022/0263104 A1 | 8/2022 | Chiang et al. |
| 2022/0263193 A1 | 8/2022 | Chen et al. |
| 2022/0278427 A1 | 9/2022 | Lawrence et al. |
| 2022/0285669 A1 | 9/2022 | Doherty et al. |
| 2022/0323445 A1 | 10/2022 | Peloso et al. |
| 2022/0323550 A1 | 10/2022 | Peloso |
| 2022/0409620 A1 | 12/2022 | Kent et al. |
| 2023/0018078 A1 | 1/2023 | Slocum et al. |
| 2023/0028134 A1 | 1/2023 | Rosario-Jansen et al. |
| 2023/0034252 A1 | 2/2023 | Hartman et al. |
| 2023/0173035 A1 | 6/2023 | Kent et al. |
| 2023/0251247 A1 | 8/2023 | Rosario-Jansen et al. |
| 2023/0301999 A1 | 9/2023 | Peloso et al. |
| 2024/0026312 A1 | 1/2024 | Fischer et al. |
| 2024/0033331 A1 | 2/2024 | Kent et al. |

FOREIGN PATENT DOCUMENTS

| | | |
|---|---|---|
| CN | 1571882 A | 1/2005 |
| CN | 1598994 A | 3/2005 |
| CN | 101103509 A | 1/2008 |
| CN | 101595546 A | 12/2009 |
| CN | 101617419 A | 12/2009 |
| CN | 102460771 A | 5/2012 |
| CN | 102483046 A | 5/2012 |
| CN | 102800525 A | 11/2012 |
| CN | 106953059 A | 7/2017 |
| EP | 3279974 A1 | 2/2018 |
| KR | 20130064465 A | 6/2013 |
| KR | 20140012264 A | 2/2014 |
| TW | 533641 B | 5/2003 |
| WO | WO-2010151831 A1 | 12/2010 |
| WO | WO-2013132228 A1 | 9/2013 |
| WO | WO-2016049213 A1 | 3/2016 |
| WO | WO-2016132119 A1 | 8/2016 |
| WO | WO-2017156513 A1 | 9/2017 |
| WO | WO 2018/089808 * | 5/2018 |
| WO | WO-2019136467 A1 | 7/2019 |

OTHER PUBLICATIONS

Bessen SY, et al "Recapture and improved outcome of pegloticase response with methotrexate—A report of two cases and review of the literature" Seminars in Arthritis and Rheumatism, Aug. 2019 (ePub Dec. 4, 2018),49(1),pp. 56-61; (ePub Dec. 4, 2018) doi: 10.1016/j.semarthrit.2018.11.006. (Year: 2018).*

Alvarez-Hernandez et al., "Validation of the health assessment questionnaire disability index in patients with gout," Arthritis & Rheumatism, May 2008, vol. 59, No. 5, pp. 665-669.

Cipolleta E., et al., "Association between gout flare and subsequent cardiovascular events among patients with gout," JAMA, Aug. 2022, 328(5), pp. 440-450.

Cipolleta, E., et al., "Risk of venous thromboembolism with gout flares," Arthritis & Rheumatology, Feb. 2023, 75(9): 1638-1647.

Document "Study NCT03303989 as of Oct. 30, 2018" is a pdf of the webpage at ClinicaiTrials.gov at https://classic.clinicaltrials.gov/ct2/history/NCT03303989?A=7&8=7&C=merged#StudyPageTop documenting what was available online as of Oct. 30, 2018, accessed Sep. 14, 2023 (Year: 2018), 10 pages.

Van Groen et al., "Application of the health assessment questionnaire disability index to various rheumatic diseases," Quality of Life Research, Nov. 2010, 19, pp. 1255-1263.

Cannarella, J. et al., "Stress evolution and capacity fade in constrained lithium-ion pouch cells," Journal of Power Sources, vol. 245, Jul. 2013, pp. 745-751.

Extended European Search Report for European Application No. 18748587.5, mailed Feb. 8, 2021, 13 pages.

Final Office Action for U.S. Appl. No. 15/886,281, mailed on Dec. 30, 2021, 20 Pages.

Final Office Action for U.S. Appl. No. 16/048,765, mailed on Mar. 10, 2021, 9 pages.

International Preliminary Report on Patentability for International Application No. PCT/US2020/049691, mailed Mar. 8, 2022, 7 pages.

International Search Report and Written Opinion for International Application No. PCT/US2020/049691, mailed Dec. 15, 2020, 9 pages.

International Search Report and Written Opinion for International Application No. PCT/US2018/016406, mailed May 18, 2018, 11 pages.

International Search Report and Written Opinion for International Application No. PCT/US2018/025375, mailed Jun. 27, 2018, 7 pages.

International Search Report and Written Opinion for International Application No. PCT/US2018/044378, mailed Oct. 15, 2018, 8 pages.

Non-final Office Action for U.S. Appl. No. 16/048,765, mailed Nov. 15, 2021, 9 pages.

Non-Final Office Action for U.S. Appl. No. 15/886,281, mailed on Jun. 3, 2021, 26 pages.

Notice of Allowance for U.S. Appl. No. 16/048,765, mailed Jun. 15, 2022, 7 pages.

Notice of Allowance for U.S. Appl. No. 15/886,281, mailed Sep. 12, 2022, 8 pages.

Notice of Allowance for U.S. Appl. No. 16/048,765, dated Jul. 27, 2022, 4 pages.

Office Action for Chinese Application No. 201880018682.5, mailed Jul. 19, 2022, 28 pages.

Office Action for Chinese Application No. 201880061848.1, mailed Aug. 3, 2021, 23 pages.

Office Action for U.S. Appl. No. 15/886,281, mailed Aug. 10, 2020, 26 pages.

Office Action for U.S. Appl. No. 15/886,281, mailed Dec. 16, 2019, 15 pages.

Office Action for U.S. Appl. No. 15/941,673, mailed Dec. 10, 2019, 7 pages.

Office Action for U.S. Appl. No. 16/048,765, mailed Dec. 11, 2020, 6 pages.

Office Action for U.S. Appl. No. 16/104,480, mailed Apr. 17, 2020, 10 pages.

Office Action mailed Sep. 26, 2021, for Chinese Application No. 201880018682.5, 7 pages.

Partial Supplementary European Search Report for European Application No. 18748587.5, mailed Nov. 6, 2020, 11 pages.

Restriction Requirement for U.S. Appl. No. 17/339,326, mailed Jan. 27, 2023, 6 pages.

"IMURAN (azathioprine)," Product Information, Reference ID: 2951014, Prometheus Laboratories Inc., May 2011, 9 pages.

* cited by examiner

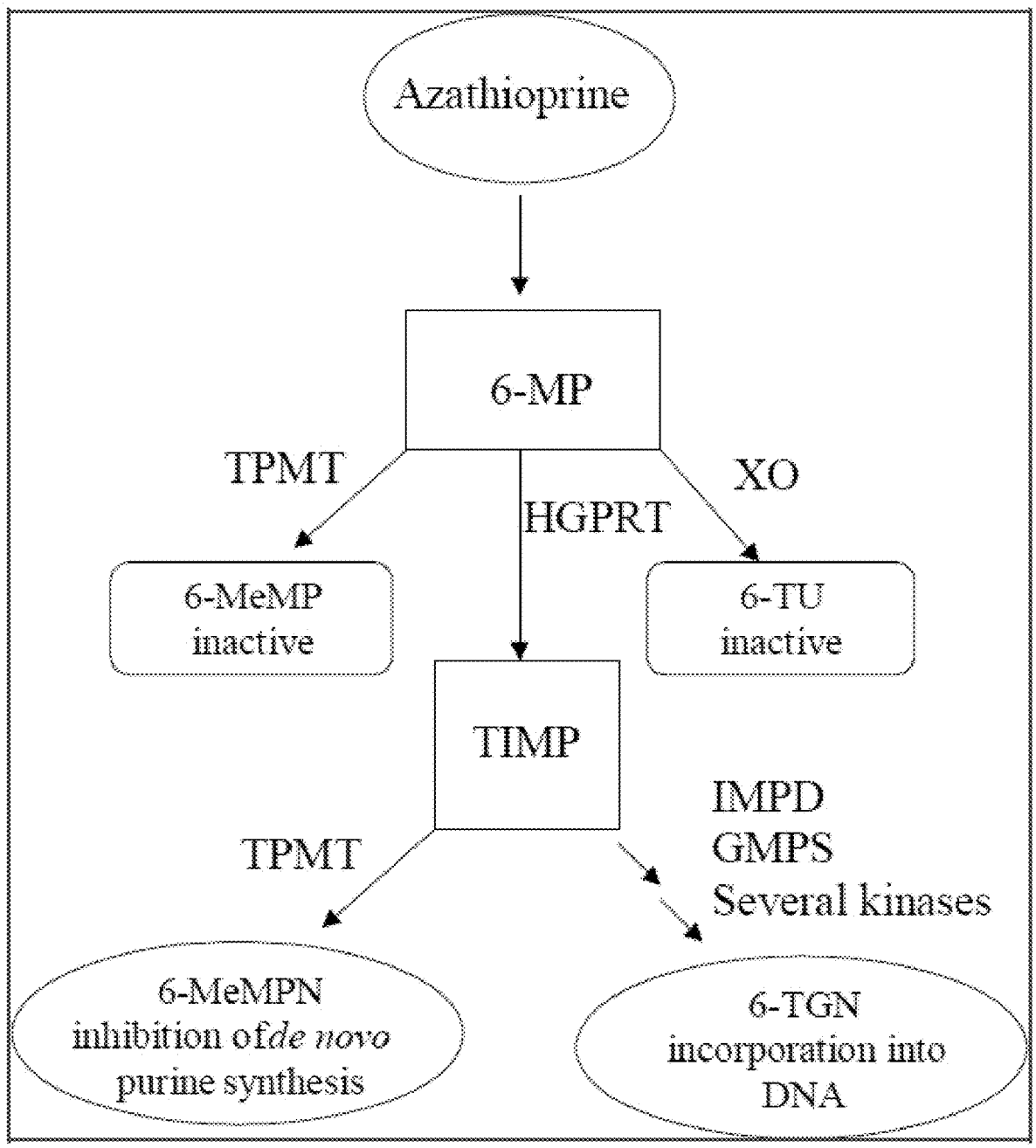

METHODS FOR TREATING GOUT

CROSS REFERENCE TO RELATED APPLICATIONS

This application claims the benefit of U.S. Provisional Patent Application No. 62/798,782, filed Jan. 30, 2019, and U.S. Provisional Patent Application No. 62/903,562, filed Sep. 20, 2019, which are incorporated by reference herein in their entireties.

FIELD OF THE DISCLOSURE

Gout affects approximately 4% of the U.S. population, is the most common form of inflammatory arthritis in men, and is associated with decreased quality of life. The frequency of gout is increasing worldwide, with prevalence rates estimated to be as high as 7% in older men. It is estimated that up to 400,000 (up to 5% of the estimated 8 million persons with gout) in the United States experience chronic refractory gout, characterized by ongoing symptoms of active disease and a failure to control/maintain serum urate (SUA)<6 mg/dL with conventional xanthine oxidase inhibitors (i.e. allopurinol and febuxostat) and uricosuric agents (i.e. probenecid). These patients often have significant, disabling urate deposits in soft tissues and bone known as tophi.

Uric acid (UA) is the end metabolite in the human purine catabolic pathway. When the concentration of serum uric acid (SUA) is above the biochemical limit of solubility, 6.8 mg/dL, monosodium urate crystals may precipitate in tissues. It is hypothesized that after many years of persistent hyperuricemia, accumulation of monosodium urate crystals causes symptoms of gout, such as acute inflammation of joints (gout flare), formation of gout tophi, gouty arthritis, and UA nephropathy (including UA renal stones). Control of chronic gout cannot be achieved without maintaining SUA<6 mg/dL. A total of 8.3 million patients have been diagnosed with gout in the United States. The principal pharmaceutical approach to the treatment of gout is the use of the xanthine oxidase inhibitors, allopurinol, and febuxostat, to block the synthesis of UA. Approximately 2% of patients treated with allopurinol develop allergic reactions and a severe hypersensitivity syndrome occurs in about 0.4% of the patients. Patients with medical contraindications to xanthine oxidase inhibitors because of allergy/hypersensitivity, or who have failed to normalize SUA at maximum medically appropriate doses of these medications, can go on to develop chronic gout.

Pegloticase or PEGylated uricase (KRYSTEXXA®; "KXX") is a monomethoxypoly(ethylene glycol) (PEG) modified recombinant mammalian uricase (urate oxidase) which reduces levels of UA in the serum (or plasma) by catalyzing its conversion to allantoin, a water-soluble metabolite more readily excreted in the urine than uric acid. Pegloticase provides a new therapeutic mechanism to reduce SUA in patients with chronic gout refractory to conventional oral therapy. These patients experience a severe burden of gout disease characterized by tophi (approximately 70%), frequent and often crippling flares (approximately 7 per year), and deforming arthritis. Pegloticase provides medical benefits in patients who respond by lowering SUA and by reducing tophus burden in these patients who currently have no therapeutic options.

Seven clinical studies have been conducted with pegloticase in patients with refractory chronic gout. The Phase 1 program established an acceptable profile of tolerability and safety for intravenous (IV) dosing, whereas subcutaneous dose administration was less well tolerated. The Phase 2 program identified a minimally effective dose (4 mg), a dose-response plateau dose (12 mg), a safe and optimally effective dose (8 mg), and a once every 2 weeks or once every 4 weeks dosing regimen.

Two randomized, double-blind, placebo-controlled, multi-center, 6-month safety and efficacy Phase 3 studies have been conducted in a total of 225 hyperuricemic patients (SUA>8 mg/dL) with symptomatic gout who reported contraindication to or who had failed to normalize SUA with allopurinol therapy. The pooled efficacy results showed improvements in tophus burden consistent with urate-lowering effect of pegloticase in both dose groups. Improvements were more rapid in patients who received pegloticase 8 mg every 2 weeks compared to every 4 weeks and met the outcomes data of complete resolution of at least 1 tophus with no new or progressive tophi as assessed by blinded assessment of digital photographs of target tophi.

The pooled safety results from these Phase 3 studies showed that gout flares were more common in the pegloticase groups than in the placebo group during the first 3 months of therapy, a physiological effect resulting from SUA-lowering which is commonly observed upon the initiation of all urate-lowering therapies. During the second 3 months of treatment, a lower proportion of pegloticase-treated patients experienced flares than patients receiving placebo. The incidence of flares during this time period was lowest in the group receiving pegloticase 8 mg every 2 weeks than in the group who received pegloticase 8 mg every 4 weeks, as was the incidence of infusion-related reactions (26% with biweekly dosing vs. 40% with the every-4-week dosing regimen). Both infusion reactions (IRs) and gout flares were least common in patients with sustained urate-lowering responses to treatment and those who received bi-weekly treatment. In most pegloticase-treated patients with IRs, a loss of response to pegloticase (return to SUA>6 mg/dL) preceded the time of the first IR (20/21; 95%).

A relationship between the loss of urate-lowering efficacy, incidence of IRs, and high-titer antibody formation was identified in a post-hoc analysis of the pooled data from the Phase 3 studies. Patients with high anti-pegloticase antibody titers (>1:2430) showed a loss of pegloticase activity attributed to a more rapid clearance of drug in the presence of these antibodies. In one study, 69 (41%) of 169 patients receiving pegloticase developed high titer anti-pegloticase antibodies and subsequently lost response to the drug. In a second study, only 1 of 52 participants with high antibody titers maintained a response to pegloticase (serum urate <6 mg/dL). In addition, 60% participants with high titers developed IR. Anti-pegloticase antibodies were largely directed to the polyethylene glycol (PEG) portion of the molecule and altered the pharmacokinetic clearance of pegloticase, resulting in inhibition of SUA lowering activity. In another study, only 7 of 65 patients (10.8%) with an antibody titer exceeding 1:2430 at any time during treatment maintained a response to pegloticase compared with 89.2% (58/65) who had never had an antibody titer above that level. In addition, 31 of 52 (60%) patients with titers exceeding 1:2430 developed IRs. The ability of pegloticase to induce antibody production demonstrated the antigenic potential of the drug, and thus raised the possibility that relatively large or more frequent doses of pegloticase (antigen) might reduce antibody formation by induction of antigen-specific non-responsiveness (high zone tolerance). By preventing the formation of anti-pegloticase antibodies, a tolerizing dose regimen should prevent loss of response to the drug and decrease the incidence of IRs associated with it.

As described herein, an alternate approach to prevent immunogenicity by pegloticase and therefore reduce the incidence of IRs, is co-administration of pegloticase and an immunosuppressive agent. As described herein, one such immunosuppressive agent is azathioprine (AZA) immunosuppressive therapy.

The long-term safety of pegloticase has been demonstrated in an open-label extension study that enrolled 151 patients: 149 received pegloticase either bi-weekly or every 4 weeks for up to 30 months and 2 chose observation only. No new safety signals were observed and ongoing patient benefit in a number of clinical outcome measures was maintained beyond the 6-month period of the double-blind studies.

In one aspect, the disclosure provides a method of treating gout in a patient weighing <120 kg and having a serum uric acid level of ≥6 mg/dL comprising: administering a PEGylated uricase to said patient at a tolerizing dosage regimen, said tolerizing dosage regimen comprising 8 mg intravenously on a weekly basis for 3 weeks for a total of 3 doses; and after the tolerizing dosage regimen, administering the PEGylated uricase at a dosage of 8 mg intravenously every 2 weeks for a total of 11 doses.

In another aspect, the disclosure provides a method of treating gout in a patient weighing ≥120 kg and having a serum uric acid level of ≥6 mg/dL comprising: administering a PEGylated uricase to said patient at a tolerizing dosage regimen, said tolerizing dosage regimen comprising 8 mg, 12 mg, or 16 mg intravenously at the first week of treatment for a total of one dose, followed by 8 mg intravenously on a weekly basis for 2 weeks after the first week of treatment, for a total of 2 doses; and after the tolerizing dosage regimen, administering the PEGylated uricase at a dosage of 8 mg intravenously every 2 weeks for a total of 11 doses.

In another aspect, the disclosure provides a method of treating gout in a patient weighing <120 kg and having a serum uric acid level of ≥6 mg/dL comprising: co-administering a PEGylated uricase and azathioprine (AZA) immunosuppressive therapy to said patient using a dosage regimen comprising a dose of 8 mg of the PEGylated uricase intravenously every 2 weeks for a total of 13 doses; and a dose of 1.25 mg/kg AZA orally daily for one week, for a total of 7 doses, followed by 2.5 mg/kg orally daily, wherein the AZA immunosuppressive therapy is initiated 2 weeks prior to the first dose of the PEGylated uricase and continued through the duration of the PEGylated uricase treatment.

In another aspect, the disclosure provides a method of reducing or preventing loss of response to a PEGylated uricase and prolonging the urate lowering effect comprising co-administration of the PEGylated uricase at a dosage of 8 mg intravenously every 2 weeks, and azathioprine (AZA) at a dosage of 2.5 mg/kg daily to a patient having a serum uric acid level of ≥6 mg/dL prior to PEGylated uricase treatment initiation; wherein the administration of the PEGylated uricase and AZA result in the serum uric acid level being normalized relative to a patient not receiving co-administration of the PEGylated uricase and AZA immunosuppressive therapy.

In one embodiment, any of such methods further comprise measuring one or more of trough PEGylated uricase levels, anti-PEGylated uricase antibody levels, and anti-PEG antibody levels, prior to each dose of the PEGylated uricase after the first dose.

In another embodiment, any of such methods further comprise measuring trough AZA metabolite levels prior to each dose of the PEGylated uricase.

In another embodiment, any of such methods further comprise measuring serum uric acid (SUA) levels, hematology, and/or liver function tests on a weekly basis during treatment. In another embodiment, blood tests may be performed every other week, or every third week. For example, blood tests may be performed at screening, at weeks 0 (baseline), 3, 5, 7, 9, 11, 13, 15, 17, 19, 21, 23. In some embodiments, a blood test as described herein may be performed on the same day each week, or may be performed within 1 or 2 days of the previous blood test performed. Blood tests may be drawn for any blood tests described herein within 24 hours prior to administration of KXX.

For determination of serum uric acid, if the SUA is >6 mg/dL, the subject may not be dosed and the SUA may be repeated. In some embodiments, if the SUA is >6 mg/dL, a subject may be withdrawn from the study. In other embodiments, samples that result in discordant results between laboratories may be evaluated to discuss whether the subject should continue on study drug or discontinue dosing.

In another embodiment, said co-administration of the PEGylated uricase and AZA immunosuppressive therapy results in normalization of the serum uric acid level in the patient relative to a patient not receiving co-administration of the PEGylated uricase and AZA immunosuppressive therapy.

In another embodiment, the serum uric acid level is reduced to less than 6 mg/dL as a result of co-administration of the PEGylated uricase and AZA immunosuppressive therapy. In another embodiment, the serum uric acid level is reduced to less than 5 mg/dL as a result of co-administration of the PEGylated uricase and AZA immunosuppressive therapy. In another embodiment, the serum uric acid level is reduced to less than 2 mg/dL as a result of co-administration of the PEGylated uricase and AZA immunosuppressive therapy.

In another embodiment, the incidence of infusion reaction, gout flare, or anaphylaxis is reduced as a result of co-administration of the PEGylated uricase and AZA immunosuppressive therapy.

In another embodiment, the level of AZA metabolite is increased relative to a patient not receiving co-administration of the PEGylated uricase and AZA immunosuppressive therapy.

In another embodiment, any of the methods described herein further comprise measuring one or more of peripheral joint urate deposition volume and inflammatory volume.

In another embodiment, peripheral joint urate deposition volume is reduced in the patient relative to a patient not receiving co-administration of the PEGylated uricase and AZA immunosuppressive therapy. In another embodiment, peripheral joint urate deposition volume is determined by dual-energy computed tomography (DECT) scanning.

In another embodiment, inflammatory volume is reduced in the patient relative to a patient not receiving co-administration of the PEGylated uricase and AZA immunosuppressive therapy. In another embodiment, inflammatory volume is determined by Dynamic Contrast Enhanced—Magnetic Resonance Imaging (DCE-MRI) or MRI without contrast, or both.

In another embodiment, the mean titer of anti-PEGylated uricase antibodies is less than or equal to 1:7000 as a result of co-administration of the PEGylated uricase and AZA immunosuppressive therapy.

In another embodiment, the serum uric acid level is normalized by week 17 after co-administration of the PEGylated uricase and AZA immunosuppressive therapy begins.

These and other embodiments of the disclosure are described in detail below.

BRIEF DESCRIPTION OF THE DRAWINGS

FIG. 1 shows the metabolism pathway of azathioprine (AZA): competing pathways result in inactivation by TPMT or XO, or incorporation of cytotoxic nucleotides into DNA. GMPS: Guanosine monophosphate synthetase; HGPRT: Hypoxanthine-guanine-phosphoribosyl-transferase; IMPD: Inosine monophosphate dehydrogenase; MeMP: Methylmercaptopurine; MeMPN: Methylmercaptopurine nucleotide; TGN: Thioguanine nucleotides; TIMP: Thioinosine monophosphate; TPMT: Thiopurine S-methyltransferase; TU Thiouric acid; XO: Xanthine oxidase.

DETAILED DESCRIPTION

Overview

In one embodiment, the disclosure provides a method of treating gout in a patient weighing <120 kg and having a serum uric acid level of ≥6 mg/dL comprising: administering a PEGylated uricase to said patient at a tolerizing dosage regimen, wherein the tolerizing dosage regimen comprises 8 mg intravenously on a weekly basis for 3 weeks for a total of 3 doses; and after the tolerizing dosage regimen, administering the PEGylated uricase at a dosage of 8 mg intravenously every 2 weeks for a total of 11 doses. In another embodiment, the disclosure provides a method of treating gout in a patient weighing ≥120 kg and having a serum uric acid level of ≥6 mg/dL comprising: administering a PEGylated uricase to said patient at a tolerizing dosage regimen comprising 8 mg, 12 mg, or 16 mg intravenously at the first week of treatment for a total of one dose, followed by 8 mg intravenously on a weekly basis for 2 weeks after the first week of treatment, for a total of 2 doses; and after the tolerizing dosage regimen, administering the PEGylated uricase at a dosage of 8 mg intravenously every 2 weeks for a total of 11 doses. In another embodiment, the disclosure provides a method of treating gout in a patient weighing <120 kg and having a serum uric acid level of ≥6 mg/dL prior to PEGylated uricase treatment initiation, comprising: co-administering a PEGylated uricase and azathioprine (AZA) immunosuppressive therapy to said patient using a dosage regimen comprising a dose of 8 mg of the PEGylated uricase intravenously every 2 weeks for a total of 13 doses; and a dose of 1.25 mg/kg AZA orally daily for one week, for a total of 7 doses, followed by 2.5 mg/kg orally daily, wherein the AZA immunosuppressive therapy is initiated 2 weeks prior to the first dose of the PEGylated uricase and continued through the duration of the PEGylated uricase treatment. In another embodiment, the disclosure provides a method of reducing or preventing loss of response to a PEGylated uricase and prolonging the urate lowering effect comprising co-administration of the PEGylated uricase and AZA immunosuppressive therapy to a patient having a serum uric acid level of ≥6 mg/dL prior to PEGylated uricase treatment initiation; wherein the serum uric acid level is normalized relative to a patient not receiving the PEGylated uricase and AZA immunosuppressive therapy.

KRYSTEXXA® (Pegloticase)

Pegloticase or PEGylated uricase (KRYSTEXXA®; "KXX,") is a uric acid specific enzyme, which is a PEGylated product that consists of recombinant modified mammalian urate oxidase (uricase) produced by a genetically modified strain of *Escherichia coli*. KXX is indicated for the treatment of chronic gout in patients refractory to conventional therapy. KXX is described at least in U.S. Pat. Nos. 8,188,224; 7,811,800; 9,534,013; 6,576,235; 9,377,454; 6,783,965; as well as PCT Publ. No. WO 2018/089808, each of which is incorporated herein in its entirety. In some embodiments, non-mammalian uricases may be used as deemed appropriate, or a uricase from any species. In other embodiments, muteins of a uricase as described herein, having an altered amino acid sequence, may be used and are encompassed within the present disclosure.

Certain uricases are useful for preparing conjugates with various forms of poly(ethylene glycol) or poly(ethylene oxide) (both referred to as PEG) to produce therapeutically efficacious forms of uricase having increased protein half-life and reduced immunogenicity. Thus, in some embodiments, uricase is covalently conjugated to monomethoxypoly(ethylene glycol) [mPEG] (10 kDa molecular weight). The cDNA coding for uricase is based on mammalian sequences. Each uricase subunit has a molecular weight of approximately 34 kDa per subunit. The average molecular weight of pegloticase (tetrameric enzyme conjugated to mPEG) is approximately 540 kDa.

In some embodiments, a uricase as described herein may be conjugated to any desired number of PEG or mPEG molecules, such as 1, 2, 3, 4, 5, 6, 7, 8, 9, 10, 11, 12, 13, 14, or the like. In other embodiments, a uricase as described herein may be conjugated to other modifiers in addition to, or alternatively to, PEG or mPEG. Such PEG or mPEG molecules may be attached to a uricase using any means appropriate in accordance with the disclosure. For example, a PEG or mPEG molecule may be conjugated to a uricase as described herein by a cysteine residue, or a serine residue, or a lysine residue. A PEG or mPEG may be attached to a uricase as described herein using any specific amino acid in accordance with the disclosure.

In other embodiments, a uricase of the present disclosure may be modified with a non-PEG modification. For example, one or more residues of proline, alanine, and/or serine (PAS), or combinations thereof, referred to herein as PASylation. In other embodiments, a uricase as described herein may be modified by conjugation with an antibody, a protein, or a small molecule, or may be conjugated to poly(2-ethyl-2-oxazoline) referred to herein as POZylation. In other embodiments, a uricase may be modified at the amine end or the carboxy end, or both. In other embodiments, any other modifiers deemed appropriate may be used to extend the half-life in circulation in accordance with the present disclosure.

Mode of Action of KXX

KXX achieves its therapeutic effect by catalyzing the oxidation of uric acid to allantoin, thereby lowering serum uric acid. Allantoin is an inert and water-soluble purine metabolite. It is readily eliminated, primarily by renal excretion.

KXX (pegloticase) concentrations are expressed as concentrations of uricase protein. Each mL of KXX contains 8 mg of uricase protein (conjugated to 24 mg of 10 kDa mPEG), 2.18 mg Disodium Hydrogen Phosphate Dihydrate ($Na_2HPO_4 \cdot 2H_2O$), 8.77 mg Sodium Chloride (NaCl), 0.43 mg Sodium Dihydrogen Phosphate Dihydrate ($NaH_2PO_4 \cdot 2H_2O$), and Water for Injection to deliver 8 mg of pegloticase (as uricase protein).

KXX was granted orphan designation by the FDA on Feb. 21, 2001 (ODA #00-1356) and KXX 8 mg every 2 weeks by IV infusion was approved by the United States (US) FDA on Sep. 14, 2010 for the treatment of adult patients with chronic gout refractory to conventional therapy. Since pegloticase was approved in the US, there have been no new safety signals reported to Horizon Pharma, PLC (Horizon) the manufacturer of KXX. The most common adverse events continue to be IRs, anaphylaxis, and gout flares. Post-marketing safety information suggests that the concomitant use of pegloticase with urate-lowering agents may mask the detection of patients who have lost therapeutic response to the drug and increase the risk of IR and/or anaphylaxis. Pegloticase is contraindicated in patients with glucose-6-phosphate dehydrogenase (G6PD) deficiency because of the risk of hemolysis and methemoglobinemia.

Treatment of Patients with KXX

KXX treatment may be initiated with monitoring of serum uric acid (SUA) levels prior to each infusion. In some embodiments, KXX therapy may be discontinued if the SUA levels increase to above 6 mg/dL, particularly when 2 consecutive levels above 6 mg/dL are observed.

In addition, in order to reduce the incidence of infusion reactions, adverse events (AEs), such as gout flare, or serious adverse events (SAEs) such as anaphylaxis, patients may be pre-medicated with antihistamines and/or corticosteroids. AEs and SAEs are described in detail below. Anaphylaxis or other IRs may occur with any infusion, including a first infusion, or any subsequent infusion, and generally manifests within 2 hours of the infusion. Delayed-type hypersensitivity reactions may also occur. The most common adverse reactions (occurring in about 5% or more of KXX-treated patients) are gout flares, infusion reactions, nausea, contusion or ecchymosis, nasopharyngitis, constipation, chest pain, anaphylaxis, and vomiting. Additional monitoring of patients during and after infusion may be beneficial to prevent or detect such reactions. In some embodiments, patients are monitored for one hour or more following administration of KXX. In some embodiments, gout flare prophylaxis may be recommended for patients when treating with KXX. For example, gout flare prophylaxis may be recommended for a period of about the first six months of KXX therapy.

In some embodiments, patients or subjects receiving KXX therapy, either alone or co-administered with an immunosuppressive agent, may experience exacerbation of congestive heart failure. For such patients, close monitoring after infusion may be beneficial.

In some embodiments, and in order to prevent or manage reactions to KXX therapy, such as anaphylaxis and/or infusion reactions, KXX may be administered in a healthcare setting and by a healthcare provider. The KXX admixture may be administered by intravenous infusion over a minimum of 120 minutes via gravity feed, syringe-type pump, or infusion pump. As described in detail below, KXX may be administered alone to a patient, or may be co-administered to a patient or subject with an immunosuppressive agent such as azathioprine (AZA). In some embodiments, KXX may be administered in a healthcare setting as described herein, and an immunosuppressive agent may be administered at home. In other embodiments, both KXX and an immunosuppressive agent such as AZA may be administered in a healthcare setting.

In some embodiments, pre-screening of patients or subjects to be administered KXX, either alone of co-administered with an immunosuppressive agent, such as AZA, for the presence of, or a risk for developing glucose-6-phosphate dehydrogenase (G6PD) deficiency may be beneficial. Such patients may be excluded from treatment with KXX because of a risk of hemolysis and/or methemoglobinemia.

In some embodiments, KXX, either alone, or in combination with an immunosuppressive agent or therapy, may be used to treat a patient with gout as described herein. In other embodiments, KXX may be used to treat other diseases involving the kidney, such as including, but not limited to, nephritis.

Dosage of KXX

The recommended dose and regimen of KXX for adult patients is 8 mg (uricase protein) given as an intravenous (IV) infusion every two weeks. The optimal treatment duration with KXX has not been established. KXX is a sterile, clear, colorless solution containing 8 mg/mL pegloticase in phosphate-buffered saline, and it intended for intravenous infusion.

Dosage Forms of KXX

KXX may be provided in a 1-mL sterile concentrate for dilution containing 8 mg of pegloticase protein, expressed in uricase protein amounts.

Azathioprine (AZA)

In some embodiments, azathioprine (AZA) may be administered to patients receiving KXX in order to prevent the formation of anti-KXX antibodies. Development of anti-KXX antibodies may increase the clearance of KXX, thereby causing loss of a drug response in the patient. AZA is an imidazole derivative of 6-mercaptopurine functioning as an immunosuppressive antimetabolite. Oral AZA is indicated as an adjunct for the prevention of rejection in renal homotransplantations and for the management of active rheumatoid arthritis to reduce signs and symptoms. AZA is well absorbed after oral administration, readily crosses cell membranes, and is converted intracellularly into a number of purine thioanalogues, which include the main active nucleotide, thioinosinic acid. AZA suppresses disease manifestations as well as underlying pathology in animal models of autoimmune disease. However, the mechanism by which AZA affects autoimmune disease is unknown. Risks associated with AZA include cytopenias, malignancy, and serious infections. Other common side effects include nauseas and vomiting. Patients with intermediate thiopurine S-methyl transferase (TPMT) activity may be at an increased risk of myelotoxicity if receiving conventional doses of AZA. Patients with low or absent TPMT activity are at an increased risk of developing severe, life-threatening myelotoxicity if receiving conventional doses of AZA. Subjects with a homozygous TPMT variant genotype will be excluded from the trial. AZA may also be referred to herein as IMURAN®.

In accordance with the disclosure, AZA may be administered as an oral tablet. Each scored tablet contains 50 mg azathioprine and the inactive ingredients lactose, magnesium stearate, potato starch, povidone, and stearic acid.

In some embodiments, the dosage of AZA used in the present study is 1.25 mg/kg daily, administered orally. In some embodiments, AZA may be administered at a dosage of 2.5 mg/kg daily, administered orally. Such a dosage may be administered to a patient to prevent or control immunogenicity to KXX or associated AEs, SAEs, or IRs occurring as a result of KXX treatment. In some embodiments, AZA may be administered to a patient starting when the serum uric acid level is greater than 6 mg/dL. Alternate dosages of AZA may be used as deemed appropriate by a clinician. For example, AZA may be administered at a dosage of 1 mg/kg, 1.05 mg/kg, 1.1 mg/kg, 1.15 mg/kg, 1.2 mg/kg, 1.25 mg/kg, 1.3 mg/kg, 1.35 mg/kg, 1.4 mg/kg, 1.45 mg/kg, 1.5 mg/kg, 1.55 mg/kg, 1.6 mg/kg, 1.65 mg/kg, 1.7 mg/kg, 1.75 mg/kg, 1.8 mg/kg, 1.85 mg/kg, 1.9 mg/kg, 1.95 mg/kg, 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5 mg/kg, 5.1 mg/kg, 5.2 mg/kg, 5.3 mg/kg, 5.4 mg/kg, 5.5 mg/kg, or the like. One of skill in the art will understand that dosages of drugs as described herein may be altered as needed for a patient or subject without deviating from the scope of the disclosure.

In other embodiments, AZA may be administered once per day, twice per day, 3 times per day, or more times per day as needed. In other embodiments, AZA may be administered every 2 days, or every 3 days, or every 4 days, or every 5 days, or every 6 days, or every 7 days, or every 8 days, or every 9 days, or every 10 days, or every 11 days, or every 12 days, or every 13 days, or every 14 days. In other embodiments, the drug may be administered one per week, twice per week, 3 times per week, 4 times per week, 5 times per week, 6 times per week, 7 times per week, 8 times per week, 9 times per week, 10 times per week, 11 times per week, 12 times per week, 13 times per week, 14 times per week, or the like. In some embodiments, different dosages or frequencies may be used on different days, as described herein.

Azathioprine is chemically 6-[(1-methyl-4-nitro-1H-imidazol-5-yl)thio]-1H-purine. AZA is an imidazolyl derivative of 6-mercaptopurine and many of its biological effects are similar to those of the parent compound. AZA is insoluble in water, but may be dissolved with addition of one molar equivalent of alkali. Azathioprine is stable in solution at neutral or acid pH but hydrolysis to mercaptopurine occurs in excess sodium hydroxide (0.1N), especially on warming. Conversion to mercaptopurine also occurs in the presence of sulfhydryl compounds such as cysteine, glutathione, and hydrogen sulfide.

Clinical Pharmacology of AZA

Azathioprine is well absorbed following oral administration. Maximum serum radioactivity occurs at 1 to 2 hours after oral $^{35}$S-azathioprine and decays with a half-life of 5 hours. This is not an estimate of the half-life of azathioprine itself, but is the decay rate for all $^{35}$S-containing metabolites of the drug. Because of extensive metabolism, only a fraction of the radioactivity is present as azathioprine. Usual doses produce blood levels of azathioprine, and of mercaptopurine derived from it, which are low (<1 mcg/mL). Blood levels are of little predictive value for therapy since the magnitude and duration of clinical effects correlate with thiopurine nucleotide levels in tissues rather than with plasma drug levels. Azathioprine and mercaptopurine are moderately bound to serum proteins (30%) and are partially dialyzable.

Azathioprine is metabolized to 6-mercaptopurine (6-MP). Both compounds are rapidly eliminated from blood and are oxidized or methylated in erythrocytes and liver; no azathioprine or mercaptopurine is detectable in urine after 8 hours. Activation of 6-mercaptopurine occurs via hypoxanthine-guanine phosphoribosyl transferase (HGPRT) and a series of multi-enzymatic processes involving kinases to form 6-thioguanine nucleotides (6-TGNs) as major metabolites. The cytotoxicity of azathioprine is due, in part, to the incorporation of 6-TGN into DNA.

6-MP undergoes two major inactivation routes (see FIG. 1). One is thiol methylation, which is catalyzed by the enzyme thiopurine S-methyltransferase (TPMT), to form the inactive metabolite methyl-6-MP (6-MeMP). TPMT activity is controlled by a genetic polymorphism. For Caucasians and African Americans, approximately 10% of the population inherit one non-functional TPMT allele (heterozygous) conferring intermediate TPMT activity, and 0.3% inherit two TPMT non-functional alleles (homozygous) for low or absent TPMT activity. Non-functional alleles are less common in Asians. TPMT activity correlates inversely with 6-TGN levels in erythrocytes and presumably other hematopoietic tissues, since these cells have negligible xanthine oxidase (involved in the other inactivation pathway) activities, leaving TPMT methylation as the only inactivation pathway. Patients with intermediate TPMT activity may be at increased risk of myelotoxicity if receiving conventional doses of IMURAN®.

Patients with low or absent TPMT activity are at an increased risk of developing severe, life-threatening myelotoxicity if receiving conventional doses of IMURAN®. TPMT genotyping or phenotyping (red blood cell TPMT activity) can help identify patients who are at an increased risk for developing IMURAN® toxicity. Accurate phenotyping (red blood cell TPMT activity) results are not possible in patients who have received recent blood transfusions.

Another inactivation pathway is oxidation, which is catalyzed by xanthine oxidase (XO) to form 6-thiouric acid. The inhibition of xanthine oxidase in patients receiving allopurinol (ZYLOPRIM®) is the basis for the azathioprine dosage reduction required in these patients.

Proportions of metabolites are different in individual patients, and this presumably accounts for variable magnitude and duration of drug effects. Renal clearance is probably not important in predicting biological effectiveness or toxicities, although dose reduction is practiced in patients with poor renal function.

Pharmacokinetic (PK) Analysis

In some embodiments, patients or subjects of the present disclosure may have blood samples taken for PK analysis during treatment with KXX, either alone, or co-administered with an immunosuppressive agent, such as AZA. Although limited PK results have been reported in subjects receiving pegloticase, and no PK studies have been performed in subjects weighing ≥120 kg, the present disclosure provides PK analysis in patients receiving KXX treatment, either alone or co-administered with an immunosuppressive agent or therapy. Sundy et al. (*JAMA* 306(7):711-20, 2011) reported results from 24 subjects with refractory gout who received single doses from 0.5 to 12 mg of pegloticase. PK parameters included plasma uricase activity (pUox) and the plasma urate concentration (pUAc). In this study, the pUox half-life was 6.4 to 13.8 days. After doses of 4 to 12 mg, the pUAc fell within 24 to 72 hours, from a mean±SD value of 11.1±0.6 mg/dL to 1.0±0.5 mg/dL; the AUC value for the pUAc was equivalent to maintaining the pUAc at 1.2 to 4.7 mg/dL for 21 days post-infusion. It remains uncertain whether body mass affects drug distribution. Since pegloticase is administered as a single dose regardless of body mass, this is important to assess.

Joint Imaging

In some embodiments, joint imaging may be performed for patients or subjects receiving KXX, either alone or co-administered with immunosuppressive therapy, such as AZA. Clinical research has shown that measuring tophus volume alone in gout is incomplete as successful therapy also needs to be associated with a reduction in inflammation, chronic synovitis, acute flares and slowing the progression or even healing of bone erosion, and thus, application of all-inclusive measurements that can measure all parameters of the physiologic impact of urate deposition will allow for comprehensive assessment of chronic gout and the impact of treatment. In some embodiments, a sub-study may also be performed to assess the ability of DECT and DCE-MRI to measure treatment response to pegloticase in subjects with chronic refractory gout.

Co-Administration of KXX and Immunosuppressive Therapy

Various embodiments of the disclosure provide for treatment of gout or gout related symptoms by administering KXX, either alone or co-administered with an immunosuppressive or immunomodulatory agent. In some embodiments, KXX may be administered alone to a patient for treatment of gout. In other embodiments, KXX may be co-administered with an immunosuppressant or immunomodulatory agent, such as AZA, for a combined immunosuppressive therapy. As used herein, "immunosuppressive agent" may also be referred to as "immunosuppressant" or "immunosuppressive therapy." In some embodiments, an "immunosuppressant" may also be referred to herein as an "immunomodulatory agent."

Administration of an immunosuppressive drug may reduce or eliminate any immune reactions that may occur in the patient. An immune reaction that may be encountered in a drug treatment as described herein may be an allergic reaction or any associated symptoms, including, but not limited to, hives, itching, nasal congestion, rash, scratchy throat, watery or itchy eyes. Severe allergic reactions may have additional symptoms, including, but not limited to abdominal cramping or pain, pain or tightness in the chest, intestinal upset, dizziness, nausea, weakness, or the like. In some embodiments, a severe allergic reaction may include symptoms of anaphylaxis as described herein. Drug reactions may be referred to herein as adverse events (AEs), and may be mild AEs or may be serious AEs (SAEs). Such combination of KXX and another drug, such as AZA, may reduce adverse events in a patient or subject. Thus, in some embodiments, administration of an immunosuppressive therapy with KXX may be beneficial for patients having gout or symptoms thereof. In some embodiments, a patient or subject may be an individual having a serum uric acid level of ≥6 mg/dL prior to PEGylated uricase treatment initiation.

In some embodiments, patients or subjects weighing less than 120 kg may benefit from a particular dosage of KXX, or a particular dosage regiment, as described herein. For example, patients weighing less than 120 kg may be initially treated with a tolerizing dose of KXX, such as a dose of 8 mg KXX on a weekly basis for 3 weeks for a total of 3 doses. In some embodiments, such tolerizing dosage may be altered as deemed necessary by a clinician or practitioner.

Alternatively, for patients weighing greater than or equal to 120 kg, a tolerizing dose of KXX may include a dose of 8 mg, 12 mg, or 16 mg KXX intravenously at the first week of treatment for a total of one dose, followed by 8 mg intravenously on a weekly basis for 2 weeks after the first week of treatment, for a total of 2 doses. Such alternate dosing may be beneficial for patients having greater body weight, or a higher body mass index (BMI). In some embodiments, patients weighing greater than or equal to 120 kg may be grouped into treatment groups, with each group receiving a different tolerizing dosage of KXX. For example, one group may receive a tolerizing dose of 8 mg KXX, while another group may receive a tolerizing dose of 12 mg KXX, and still another group may receive a tolerizing dose of 16 mg KXX.

In some embodiments, KXX may be administered to a patient following a tolerizing dose at a dosage such as 8 mg by intravenous infusion every 2 weeks. This dosage may be continued for any period of time deemed appropriate by a clinician or practitioner. For example, 8 mg KXX may be given to a particular patient every 2 weeks following a tolerizing dosage regimen and lasting for a period of time totaling 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, or the like. In some embodiments, a patient may be given to a patient for more than 6 months, or more than 7 months, or more than 8 months, or more than 9 months, or more than 10 months, or more than 11 months, or more than 12 months, or more than 18 months, or more than 24 months. In other embodiments, KXX may be given to a patient for any length of time deemed appropriate by a clinician or practitioner, and as described herein, for the remainder of the patient's life.

In some embodiments, the patient may be treated with KXX plus an immunosuppressive agent or therapy for at least one month. In some embodiments, the patient is treated for 2 months, 3 months, 4 months, 5 months, 6 months, 7 months, 8 months, 9 months, 10 months, 11 months, 12 months, 15 months, 18 months, 21 months, 24 months, 30 months, 36 months, or more. In some embodiments, the patient may be treated for up to 30 weeks, or 25 weeks, or 20 weeks, or 17 weeks, or 12 weeks, or 6 weeks, or 4 weeks, or 2 weeks, or 24 months, or up to 36 months, or up to 48 months. In some embodiments, the patient may be treated for more than 24 months. In some embodiments, the patient is treated for the rest of the patient's life.

In some embodiments, a tolerizing dosage regimen as described herein may be combined with the use or co-administration of an immunosuppressive agent or therapy. Such a tolerizing dosage regimen may involve escalation of a dose of KXX and an immunosuppressive agent or therapy such that the patient or subject is able to better tolerate KXX or the dosage thereof. In other embodiments, such a tolerizing dosage regimen may involve increasing or escalating doses of KXX with a particular dose of an immunosuppressive agent or therapy. Such treatments may be employed for any duration as described herein.

In some embodiments, treatment with KXX may be continued as appropriate for any length of time, as long as the patient experiences an improvement in the symptoms or signs of gout. Such signs/symptoms of gout that may serve as a metric for improvement in disease severity may include, but are not limited to, serum uric acid level, peripheral joint urate deposition volume, and inflammatory volume. For example, KXX treatment, either alone, or co-administered with an immunosuppressive agent, such as AZA, may be monitored with regular assessment of the patient or subject before, during, and following treatment. Any number of diagnostic or evaluative testing procedures may be performed at any time, and at any frequency as deemed necessary by a clinician or practitioner.

KXX treatment typically is monitored using regular determination of the patient's SUA levels. A reduction in the serum uric acid level relative to the SUA in the patient before KXX treatment may generally be indicative of successful treatment with KXX, alone, or co-administered with an immunosuppressive agent or therapy, such as AZA, as described herein. Collection and measurement of a patient's serum uric acid levels are known to those of skill in the art. In some embodiments, the patient's serum uric acid levels are assayed before each KXX therapy. In some embodiments, any suitable method for collecting appropriate samples and methods of measuring or quantifying uric acid levels may be used in accordance with the disclosure.

Additional measurements to assess the efficacy and safety of KXX treatment may be used in accordance with the disclosure. These may include trough KXX levels, anti-KXX antibody levels, and/or anti-PEG antibody levels. In some embodiments, these measurements may be taken prior to each dose of KXX after the first dose. In other words, an initial dose of KXX may be administered to a patient without measurement of KXX levels, anti-KXX antibody levels, and/or anti-PEG antibody levels. Then, prior to each subsequent dose of KXX, such measurements may be taken as described herein. For treatment regiments wherein KXX is co-administered with an immunosuppressive agent or therapy, the same measurements may be taken at the same time periods, without deviating from the scope of the disclosure. Such measurements may be obtained from each patient as necessary in order to evaluate response to the treatment, or a lack thereof. Specific criteria for responders and non-responders to treatment with KXX are described in the Examples.

In some embodiments, when KXX is co-administered with an immunosuppressive agent or therapy, such as AZA, additional measurements for assessing the efficacy of treatment may be obtained. For example, trough azathioprine metabolite levels may be obtained for each patient or subject prior to each dose of KXX, as described herein. In other embodiments, measurement of hematology and liver function may be obtained for each patient on a weekly basis during treatment. This type of measurement may provide information to clinicians relating to the breakdown of the immunosuppressive agent in the patient's body.

In some embodiments, co-administration of KXX and AZA immunosuppressive therapy results in normalization of the serum uric acid level in the patient relative to a patient not receiving KXX and azathioprine immunosuppressive therapy. As used herein, "normalization" refers to lowering of the serum uric acid level similar to that found in normal healthy patients. In other embodiments, normalization may refer to SUA levels being reduced to levels similar to that found in patients not requiring KXX treatment or therapy. In some embodiments, the serum uric acid level is normalized by week 17 after KXX and azathioprine immunosuppressive therapy begins.

In some embodiments, as described herein, the serum uric acid level in patients treated with KXX and an immunosuppressive therapy such as AZA is reduced to less than 6 mg/dL as a result of treatment, including, but not limited to, 6 mg/dL, 5.9 mg/dL, 5.8 mg/dL, 5.7 mg/dL, 5.6 mg/dL, 5.5 mg/dL, 5.4 mg/dL, 5.3 mg/dL, 5.2 mg/dL, 5.1 mg/dL, 5 m/dL, 4.9 mg/dL, 4.8 mg/dL, 4.7 mg/dL, 4.6 mg/dL, 4.5 mg/dL, 4.4 mg/dL, 4.3 mg/dL, 4.2 mg/dL, 4.1 mg/dL, 4 mg/dL, 3.9 mg/dL, 3.8 mg/dL, 3.7 mg/dL, 3.6 mg/dL, 3.5 mg/dL, 3.4 mg/dL, 3.3 mg/dL, 3.2 mg/dL, 3.1 mg/dL, 3 mg/dL, 2.9 mg/dL, 2.8 mg/dL, 2.7 mg/dL, 2.6 mg/dL, 2.5 mg/dL, 2.4 mg/dL, 2.3 mg/dL, 2.2 mg/dL, 2.1 mg/dL, 2 mg/dL, 1.9 mg/dL, 1.8. mg/dL, 1.7 mg/dL, 1.6 mg/dL, 1.5 mg/dL, 1.4 mg/dL, 1.3 mg/dL, 1.2 mg/dL, 1.1 mg/dL, 1 mg/dL, or the like. In other embodiments, the serum uric acid level may be reduced to less than 5 mg/dL as a result of treatment. In still further embodiments, the serum uric acid level is reduced to less than 2 mg/dL as a result of KXX and azathioprine immunosuppressive therapy. Treatment with KXX plus an immunosuppressive therapy may be able to reduce the serum uric acid levels to levels that result in improvement of symptoms associated with gout as described herein.

In some embodiments, treatment of a patient or subject with KXX plus an immunosuppressive agent such as AZA results in a reduction of the incidence of infusion reaction, gout flare, or anaphylaxis.

In some embodiments, the level of azathioprine metabolite is increased relative to a patient not receiving KXX and azathioprine immunosuppressive therapy.

In some embodiments, analysis of the efficacy of a method as described herein for treating gout may further comprise measurements to assess disease severity. For example, a diagnostic imaging test, such as including, but not limited to, computed tomography (CT), magnetic resonance imaging (MRI), X-ray, ultrasound, positron emission tomography (PET), fluoroscopy, or the like.

In some embodiments, peripheral joint urate deposition volume and inflammatory volume may be measured in a patient and used to evaluate disease severity or to evaluate efficacy of the drug treatment. For example, in some embodiments, peripheral joint urate deposition volume is reduced in the patient relative to a patient not receiving KXX and AZA immunosuppressive therapy. In other embodiments, peripheral joint urate deposition volume is determined by dual-energy computed tomography (DECT) scanning. In other embodiments, inflammatory volume is reduced in the patient relative to a patient not receiving KXX and AZA immunosuppressive therapy. In other embodiments, inflammatory volume is determined by Dynamic Contrast Enhanced—Magnetic Resonance Imaging (DCE-MRI) or MRI without contrast, or both.

In some embodiments, administration of KXX alone or co-administration of KXX with an immunosuppressive therapy or agent or with a drug having monomethoxypoly (ethylene glycol) (PEG) may elicit an immune reaction in the patient or subject. Evaluation of antibodies in a subject or patient receiving KXX therapy may provide an assessment of such an immune reaction to the drug treatment. For example, in some embodiments, determination of a mean titer of anti-KXX antibodies or anti-PEG antibodies may be performed to determine an immune reaction in the patient or subject, or to determine the efficacy of immunosuppressive therapy. In some embodiments, a mean titer of anti-KXX antibodies may be determined for a patient. In other embodiments, a mean titer of anti-PEG antibodies may be determined. In some embodiments, antibody titers may be any value determined by any appropriate measurements or analyses. Antibody titers in a patient as used herein are a metric for and may indicate an immune response to a drug such as KXX. In some embodiments, an antibody titer as described herein may refer to antibodies in a patient directed against KXX or PEG. In some embodiments, an anti-KXX or anti-PEG mean antibody titer may be less than or equal to 1:7000 as a result of KXX administration. For example, an antibody titer for a patient receiving KXX therapy, either alone or in combination with AZA, may be less than or equal to about 1:100, about 1:200, about 1:300, about 1:400, about 1:500, about 1:600, about 1:700, about 1:800, about 1:900, about 1:1000, about 1:2000, about 1:3000, about 1:4000, about 1:5000, about 1:6000, about 1:7000, about 1:8000, about 1:9000, about 1:10000, or the like. In other embodiments, the antibody titers recited above may generally be found in patients who exhibit a positive response to KXX therapy (i.e., a responder). In some embodiments, a non-responder may have substantially or significantly higher antibody titers, for example, less than or equal to about 1:50000, about 1:60000, about 1:70000, about 1:80000, about 1:90000, about 1:100000, about 1:150000, about 1:200000, about 1:250000, about 1:300000, about 1:350000, about 1:400000, about 1:450000, about 1:500000, or the like. In other embodiments, such antibody titers may be determined for KXX treatment alone, or may be determined for KXX+AZA immunosuppressive therapy. Anti-KXX or anti-PEG mean antibody titers as a result of KXX and AZA immunosuppressive therapy may be beneficially maintained at or below any threshold value tolerable for the patient.

In some embodiments, anti-drug antibody titers may be reduced as a result of use of an immunosuppressive agent or therapy, such as AZA as described herein. In other embodiments, the titer of specific types of antibodies may be reduced. For example, in some embodiments, the levels or titer of any specific type of antibodies may be reduced as a result of KXX co-administered with an immunosuppressive agent or therapy, such as IgG antibodies, IgA antibodies, IgM antibodies, IgD antibodies, IgE antibodies, or combinations thereof.

In some embodiments, evaluation of antibody titers may be beneficial for patients receiving KXX, either alone, or co-administered with an immunosuppressive agent or therapy such as AZA, for the first time. In other embodiments, evaluation of antibody titers may be beneficial for patients who have developed anti-KXX antibodies, or who have been classified as non-responders to KXX treatment. Criteria for classifying a patient or subject as a responder or a non-responder are described herein elsewhere.

In some embodiments, heavier and/or younger patients may have a higher incidence of anti-KXX antibodies, or may have higher anti-KXX drug titers, than lighter and/or older patients. In other embodiments, lighter and/or older patients may have higher drug loading of KXX than heavier and/or younger patients. In some embodiments, lighter patients may have higher exposures of KXX than heavier patients. For example, in some embodiments, lighter patients may have greater than 2-fold exposure to KXX than heavier patients. In some embodiments, lower drug levels in a patient may result in anti-KXX antibodies. For example, the mean area under the curve (AUC) for lighter patients may be about 8.92 mg/L versus about 4.04 mg/L in heavier patients. In other embodiments, older patients may have higher exposures of KXX than younger patients. For example, in some embodiments, older patients may have greater than 2-fold exposure to KXX than younger patients. In some embodiments, the mean area AUC for older patients may be about 8.86 mg/L versus about 3.93 mg/L in younger patients, indicating that younger patients may have a more robust immune system. Thus, in some embodiments, additional 8-mg doses of KXX may be beneficial for younger and/or heavier patients. In other embodiments, younger and/or heavier patients may benefit from one or more loading doses of 16 mg of KXX.

In some embodiments, production of anti-drug antibodies, such as antibodies to KXX, may be reduced or eliminated by increasing the amount of KXX delivered to a patient, i.e., maintaining higher trough levels of KXX in a patient. Higher trough levels of KXX may reduce anti-drug antibody production. In some embodiments, possible dosing strategies for increasing the amount of KXX delivered to a patient, and thus producing higher trough levels in the patient, may include reducing the interval between doses of KXX, or using higher doses at the beginning of and/or during treatment. Another possible strategy for reducing anti-KXX antibodies is the use of immunomodulators, such as AZA, as described herein. Immunomodulators may reduce or eliminate an immune response to unfamiliar proteins. One of skill in the art will understand that other immunomodulators may be used with similar results, including, but not limited to, corticosteroids (i.e., prednisone), Rapimmune, myophenolate, methotrexate, or the like.

The methods disclosed herein presume that the patient is effectively receiving all of the prescribed dose. In some embodiments, depending on the age of the patient, it may be difficult to deliver a drug to a patient, for example when administering a drug to an infant and, therefore, the compliance and effectiveness of drug delivery by the patient's parent(s), guardian(s), or health care provider(s) may also be assessed.

Definitions

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As used in this specification and the appended claims, the singular forms "a," "an" and "the" include plural referents unless the context clearly dictates otherwise. Thus, for example, "an active agent" refers not only to a single active agent but also to a combination of two or more different active agents, "a dosage form" refers to a combination of dosage forms as well as to a single dosage form, and the like.

Unless defined otherwise, all technical and scientific terms used herein have the meaning commonly understood by one of ordinary skill in the art to which the disclosure pertains. Specific terminology of particular importance to the description of the present disclosure is defined below.

As used herein, an "adverse event" or "AE" refers to any untoward medical occurrence associated with the use of a drug in humans, whether or not considered drug related. An AE or suspected adverse reaction is considered a "serious adverse event" or "SAE" if, in the view of either the Investigator or Sponsor, it results in any of the following outcomes: (1) Death, (2) Life-threatening: an AE is considered "life-threatening" if, in the view of either the Investigator or Sponsor, its occurrence places the subject or subject at immediate risk of death. It does not include an AE that, had it occurred in a more severe form, might have caused death; (3) Inpatient hospitalization or prolongation of existing hospitalization; (4) A persistent or significant incapacity or substantial disruption of the ability to conduct normal life functions. (5) A congenital anomaly/birth defect; (6) Important medical events that may not result in death, be life-threatening, or require hospitalization may be considered serious when, based upon appropriate medical judgment, they may jeopardize the patient or subject and may require medical or surgical intervention to prevent one of the outcomes listed in this definition. Examples of such medical events include allergic bronchospasm requiring intensive treatment in an emergency room or at home, blood dyscrasias or convulsions that do not result in inpatient hospitalization, or the development of drug dependency or drug abuse.

As used herein, "anaphylaxis" refers to a severe, acute onset allergic reaction that may occur over minutes to several hours. Anaphylaxis may involve the skin, mucosal tissue, or both, and may have one or more symptoms including, but not limited to, generalized hives, pruritus (itching), flushing, swelling of the lips, tongue, throat or uvula, shortness of breath, vomiting, lightheadedness, wheezing, hemodynamic instability, and rash or urticaria. In addition, anaphylaxis may be accompanied by at least one of the following: respiratory compromise (e.g., dyspnea, wheeze-bronchospasm, stridor, reduced peak expiratory flow, hypoxemia), and reduced blood pressure (i.e., systolic blood pressure <90 mm Hg or greater than 30% decrease from that person's baseline) or associated symptoms of end-organ failure (e.g., hypotonia [collapse], syncope, incontinence). Anaphylaxis in accordance with the disclosure is defined by the National Institute of Allergy and Infectious Disease/Food Allergy and Anaphylaxis Network (NIAID/FAAN) clinical criteria for diagnosing anaphylaxis. Anaphylaxis reactions are reported as a serious adverse event (SAE) for the present disclosure.

As used herein, "co-administration" refers to the simultaneous administration of one or more drugs with another. For example, as described herein, co-administration of KXX with AZA may refer to administration of AZA at the same time as KXX, or may refer to administration of AZA at a specific period of time before or after KXX administration. In some embodiments, AZA may be administered before KXX. In other embodiments, KXX may be administered before AZA. In other embodiments, both drugs are administered at the same time. As described herein elsewhere, co-administration may also refer to any particular time period of administration of either KXX or AZA, or both. For example, as described herein, AZA may be administered hours, days, weeks, or months before KXX treatment. In other embodiments, AZA may be administered to a patient hours, days, weeks, or months after KXX treatment. In some embodiments, co-administration may refer to any time of administration of KXX and/or AZA such that both drugs are present in the body of a patient at the same. In some embodiments, either drug may be administered before or after the other, so long as they are both present within the patient for a sufficient amount of time that the patient received the intended clinical or pharmacological benefits.

By the terms "effective amount" and "therapeutically effective amount" of an agent, compound, drug, composition or combination which is nontoxic and effective for producing some desired therapeutic effect upon administration to a subject or patient (e.g., a human subject or patient).

As used herein, a "gout flare" refers to a manifestation of physiological or biochemical symptoms of gout, which is a possible side effect or AE associated with treatment with KXX. A gout flare may produce burning itching, tingling, or stiffness in the joints, particularly the peripheral joints. An individual may also experience redness, swelling, and pain in the joints. In accordance with the disclosure, gout flares may initially increase when starting treatment with KXX. For such individuals, medications to help reduce flares may be taken regularly for the first few months after KXX is started. Prophylactic treatment for gout flares may include, but is not limited to, colchicine or non-steroidal anti-inflammatory drugs (NSAID). In some embodiments, prophylactic treatment may be given prior to an infusion of KXX, for example one week prior to treatment with KXX.

As used herein, "glucose-6-phosphate dehydrogenase (G6PD) Deficiency" or "G6PD" refers to a condition caused by an inborn error of metabolism that predisposes an individual to red blood cell breakdown. Individuals with G6PD deficiency are not included in the present study and are generally advised not to take KXX.

As used herein, "immuno-tolerance" refers to the lack of an immune response in a patient as a result of a drug treatment such as KXX. In some embodiments, establishing immune-tolerance may also refer to reducing intolerance to KXX, or to reduce or prevent loss of a response to KXX. Such loss of response may be the result of the formation of anti-drug antibodies, which may increase clearance of KXX, causing a loss of response.

As used herein, an "infusion reaction" or "IR" refers to a reaction of a patient or subject to a drug. Infusion reactions generally refer to drugs administered by intravenous (IV) infusion. most common signs and symptoms of an infusion reaction, including urticaria (skin rash), erythema (redness of the skin), dyspnea (difficulty breathing), flushing, chest discomfort, chest pain, and rash. For the present disclosure, IRs are recorded as Infusion Reaction AEs. If the IR meets the definition for "Serious" as described herein, it is also reported as an SAE.

As used herein, "KRYSTEXXA®" or "KXX" or "pegloticase" or "PEGylated uricase" refers to a covalent conjugate of uricase produced by a genetically modified strain of Escherichia coli and monomethoxypoly (ethylene glycol). Although the term "uricase" or "PEGylated uricase" may be used herein to refer to a PEGylated uricase such as KRYSTEXXA®, one of skill in the art would understand that many different forms of a uricase may be known and used in accordance with the disclosure, and therefore any PEGylated uricase, such as KRYSTEXA or KXX, may be used for treatment of a patient with elevated SUA as described herein.

As used herein, the term "normal uric acid level" refers to a patient's blood plasma uric acid concentration in a range that does not cause physiological or biochemical symptoms or signs of gout. In some embodiments, a normal uric acid level may not exceed the biochemical limit of solubility. For females, a normal uric acid range may fall between about 2.4 mg/dL and about 6 mg dL, and for males, about 3.4 mg/dL to about 7 mg/dL. One of skill in the art will recognize that these values may vary slightly depending on the subject or patient, as well as on the laboratory. As used herein, the term "elevated uric acid levels" refers to refers to a patient's blood plasma or serum uric acid concentration equal to or greater than about 6 mg/dL. In some embodiments, the uric acid level in a patient may be normalized to less than about 6 mg/dL, or less than about 5 mg/dL, or less than about 2 mg/dL, following treatment with KXX, either alone or co-administered with an immunosuppressive agent or therapy. To this effect, uric acid levels can vary based on the particular testing methodology and from laboratory to laboratory.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" (or "active") derivative or analog, refers to a derivative or analog having the same type of pharmacological activity as the parent compound and approximately equivalent in degree. The term "pharmaceutically acceptable salts" include acid addition salts which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

As used herein, "prolonging" refers to extending the duration of the treatment effects of KXX therapy, either alone or co-administered with AZA. For example, as described herein, treatment of a patient with KXX co-administered with AZA, may result in a more enhanced response to the drug in the patient, resulting in a lowered SUA, when compared with treatment with KXX alone.

As used herein, "reducing" refers to a lowering or lessening, such as reducing drug intolerance to KXX in a patient. In some embodiments, co-administration of KXX and AZA results in "reducing" intolerance to KXX, indicating that the patient does not produce anti-KXX antibodies, or produces fewer anti-KXX antibodies than would be expected for a patient not receiving the same treatment. "Reducing" may also refer to a reduction in disease symptoms as a result of KXX treatment, either alone, or co-administered with AZA. "Reducing" intolerance to KXX may also be referred to herein as establishing, increasing, or enhancing "immuno-tolerance."

As used herein, "relatedness" or "causality" assessment is required for AEs (and SAEs) that occur during clinical investigations. The following terms will be used during this study:

Likely: Reasons to consider an AE likely related to treatment may include, but are not limited to the following: (1) Timing of the event relative to the administration of the investigational product. (2) Location of the AE relative to the site of investigational product administration. (3) Likelihood based on experience with similar products. (4) There is a biologically plausible explanation based on the mechanism of action or mode of delivery of the treatment. (5) The AE is repeated on subsequent treatments. (6) No other explanation is likely.

Severity in accordance with the disclosure is reported according to the following: Grade 1 (Mild)—No interference with daily activity. Grade 2 (Moderate)—Some interference with daily activity but medical intervention not required (e.g., doctor visit and/or medication); over the counter medicine permitted. Grade 3 (Severe)—Prevents daily activity and requires medical intervention (e.g., doctor visit and/or medication). Grade 4 (Potentially Life-threatening)—Emergency room visit or hospitalization.

As used herein, "subject" or "individual" or "patient" refers to any patient for whom or which therapy is desired, and generally refers to the recipient of the therapy.

As used herein, a "tolerizing dosage regimen" refers to a dosage or treatment regimen with KXX that induces immunological tolerance to the drug. A tolerizing dosage regimen prevents the loss of response to a drug in a patient by preventing the formation of anti-KXX antibodies. A tolerizing dosage regimen may also decrease the incidence of IRs associated with the drug.

The terms "treating" and "treatment" as used herein refer to reduction in severity and/or frequency of symptoms, elimination of symptoms and/or underlying cause, and improvement or remediation of damage. In certain aspects, the term "treating" and "treatment" as used herein refer to the prevention of the occurrence of symptoms. In other aspects, the term "treating" and "treatment" as used herein refer to the prevention of the underlying cause of symptoms associated with obesity, excess weight, and/or a related condition. The phrase "administering to a patient" refers to the process of introducing a composition or dosage form into the patient via an art-recognized means of introduction.

As used herein, "trough" refers to the lowest concentration of a drug in a patient before the next dose of the drug is administered. For example, trough KXX levels refer to the lowest levels of KXX in a patient before the next infusion of KXX. Trough levels may be used by clinicians or practitioners to determine the efficacy of the drug, or the response of the patient to the drug treatment. Trough levels of KXX or AZA may be determined or measured at any point during a treatment period as described herein, such as before any infusion of KXX, or before any administration of AZA.

Unlikely: An AE with no temporal association with the study drug but rather related to other etiologies such as concomitant medications or conditions, or subject's known clinical state.

EXAMPLES

Examples of embodiments of the present disclosure are provided in the following examples. The following examples are presented only by way of illustration and to assist one of ordinary skill in using the disclosure. The examples are not intended in any way to otherwise limit the scope of the disclosure.

Example 1—Main Study

Rationale—The present study is designed to evaluate the effect of a high zone tolerizing regimen of pegloticase on clinical outcome as defined by an SUA level <6 mg/dL at each measured time point during the study. High zone tolerance is achieved by administration of high doses of an antigen early in the period of exposure to induce antigen-specific immunosuppression. In this study, 1 extra dose of pegloticase (antigen) is administered at Week 2 of the treatment period followed by the standard bi-weekly dosing regimen for the purpose of reducing the formation of anti-pegloticase antibodies. A reduction in antibody titers is expected to decrease the incidence of IRs, thus, this endpoint will be evaluated in addition to AEs for assessment of safety. The effectiveness of the tolerizing dose regimen on clinical outcome will be evaluated against the standard bi-weekly dosing regimen from previously reported randomized controlled trials to assess whether a higher proportion of subjects will maintain SUA levels below 6 mg/dL after receiving a tolerizing regimen of pegloticase. The standard bi-weekly dosing schedule is currently approved for IV administration of pegloticase (KRYSTEXXA®; KXX) in the treatment of gout refractory to conventional therapy.

Each of the endpoints in this study is standard for assessment of the efficacy and safety of urate lowering drugs in the treatment of gout.

The primary objectives of this study are to (1) determine the response rate as measured by the normalization of serum uric acid [SUA] (<6 mg/dL) at weeks 13, 15, and 17 in subjects receiving a tolerizing regimen of pegloticase, and (2) determine the response rate as measured by the normalization of SUA (<6 mg/dL) at weeks 21, 23, and 25 in subjects receiving pegloticase and azathioprine (AZA) immunosuppressive therapy.

Secondary objectives of this study are to (1) determine the response rate as measured by the normalization of SUA (<6 mg/dL) at weeks 21, 23, and 25 in subjects receiving a tolerizing regimen of pegloticase; (2) determine the change in SUA from baseline (defined as Screening visit) to Week 17 and week 25; (3) determine the proportion of subjects with SUA<5 mg/dL at Week 17 and Week 25; (4) determine the proportion of subjects with SUA<2 mg/dL at Week 17 and Week 25; (5) assess the incidence of infusion reactions (IRs) and anaphylaxis; (6) assess the incidence and mean titer of anti-pegloticase antibodies and anti-monomethoxy-poly (ethylene glycol) (PEG) antibodies; and (7) assess the incidence of gout flares, adverse events (AEs), serious AEs (SAEs), and early terminations due to adverse events (AEs).

Exploratory objectives of this study are to (1) determine change in SUA from baseline and assess infusion reactions in subjects weighing ≥120 kg who receive one of 3 different loading doses (8, 12, and 16 mg) of pegloticase; (2) compare change in SUA from baseline and rate of infusion reactions in subjects weighing ≥120 kg and subjects weighing <120 kg; (3) characterize the pharmacokinetics (PK) of pegloticase in a subset of subjects weighing ≥120 kg and subjects weighing <120 kg and receiving loading doses of 12 and 16 mg of Pegloticase; (4) compare trough pegloticase levels in all weight and treatment groups; (5) compare trough AZA metabolite levels in subjects receiving pegloticase and AZA; (6) evaluate change from baseline in peripheral joint urate deposition volume using dual energy computed tomography (DECT) scan; (7) evaluate change from baseline in inflammatory volume using Dynamic Contrast Enhanced—Magnetic Resonance Imaging (DCE-MRI); (8) evaluate change from baseline in inflammatory volume using MRI, without contrast; and (9) compare the ability of DECT, DCE-MRI, and MRI without contrast to monitor treatment response, in a subset of subjects weighing <120 kg.

Study Design—In order to evaluate a tolerizing regimen of pegloticase (i.e., the main study), an open label, multi-center, 24-week study is performed. Eligible subjects weighing <120 kg receive pegloticase 8 mg intravenously (IV) on a weekly basis (week 1 through week 3—"Tolerizing Period"), followed by 8 mg IV every 2 weeks through week 25 for a total of 14 doses. Subjects weighing ≥120 kg are sequentially assigned to 1 of 3 different loading doses (8, 12, and 16 mg) on Study Day 1, and then receive 8 mg on weeks 2 and 3, followed by 8 mg every 2 weeks through week 25 for a total of 14 doses.

Subjects are monitored for efficacy and safety endpoints through week 25. Subjects also have blood drawn for trough pegloticase, anti-pegloticase antibody, and anti-PEG antibody levels prior to each dose on after week 1 (i.e., on weeks 2, 3, 5, 7, 9, 11, 13, 15, 17, 19, 21, 23, and 25). The study duration, per enrolled subject, will be approximately 27 weeks including a 3-week screening period, and a 24-week treatment period (End of Treatment [EOT] visit at week 25). A schematic diagram of the main study design is shown in Table 1.

TABLE 1

Main Study Design

| Study Period | Screen | Tolerizing Period-Weekly Dosing | | | Bi-weekly Dosing | | | | | | | | | | |
|---|---|---|---|---|---|---|---|---|---|---|---|---|---|---|---|
| Week | −21 days | 1 | 2 | 3 | 5 | 7 | 9 | 11 | 13 | 15 | 17 | 19 | 21 | 23 | 25 |
| Dose # | | 1 | 2 | 3 | 4 | 5 | 6 | 7 | 8 | 9 | 10 | 11 | 12 | 13 | 14 |

Up to a total of 177 evaluable subjects are planned to be evaluated in the study. Subjects who discontinue the study prematurely for reasons other than not responding to pegloticase (Non-Responder—see below) are replaced. For the main study, up to 100 subjects weighing <120 kg and 37 subjects weighing ≥120 kg (including sub-study participants) are included.

Up to 22 sites in the United States are included in the study.

Example 2—Pegloticase+AZA Immunosuppressive Therapy Arm of Study

Rationale—Although pegloticase is efficacious in reducing SUA levels and improving clinical signs and symptoms of gout, its immunogenicity led to anti-pegloticase antibody formation and associated loss of efficacy manifested by a rapid increase in SUA levels.

Immunogenicity (anti-pegloticase antibodies) in response to pegloticase therapy may give rise to low serum drug levels, loss of therapeutic response, poor drug survival, and/or AEs and IRs. The development of anti-drug antibodies can be influenced by drug- and treatment-related factors, as well as patient characteristics. A potential prophylactic strategy to manage anti-drug antibody response with biologic response modifiers is the co-administration of immune modulating therapy.

In this treatment arm, dual therapy with pegloticase and AZA immunosuppressive therapy will be evaluated in adults with chronic refractory gout with respect to prevention of immunogenicity conferred by pegloticase.

Study Design—For the pegloticase and azathioprine (AZA) arm of the study, an open label, multicenter, 24-week study is conducted. Eligible subjects weighing <120 kg will receive pegloticase 8 mg IV every 2 weeks through week 25 for a total of 13 doses. Subjects will also receive AZA (1.25 mg/kg orally daily for 1 week then 2.5 mg/kg orally daily) beginning 2 weeks prior to the first dose of pegloticase through week 25. Subjects are monitored for efficacy and safety endpoints, including hematology and liver function tests, through week 25. Subjects also have blood drawn for trough pegloticase, anti-pegloticase antibody, and anti-PEG antibody levels prior to each dose after week 1, on weeks 3, 5, 7, 9, 11, 13, 15, 17, 19, 21, 23, and 25; and sampling for trough AZA metabolite levels prior to all doses of pegloticase. The study duration, per enrolled subject, will be approximately 28 weeks including a 2-week screening period, a 2-week AZA run-in period, a 24-week treatment period (EOT visit at Week 25). A schematic diagram of the pegloticase+AZA study design is shown in Table 2.

TABLE 2

Pegloticase + AZA Study Design

| Study Period | Screen | AZA Run-in | | Bi-weekly Pegloticase Dosing | | | | | | | | | | | | |
|---|---|---|---|---|---|---|---|---|---|---|---|---|---|---|---|---|
| Week | −28 days | −14 days | −7 days | 1 | 3 | 5 | 7 | 9 | 11 | 13 | 15 | 17 | 19 | 21 | 23 | 25 |
| Pegloticase Dose # | — | — | — | 1 | 2 | 3 | 4 | 5 | 6 | 7 | 8 | 9 | 10 | 11 | 12 | 13 |
| AZA Daily Dose | — | 1.25 mg/kg | 2.5 mg/kg | 2.5 mg/kg daily | | | | | | | | | | | | |

Example 3—Sub-Studies

In addition to completing all study visits, dosing, and procedures as noted above, subsets of eligible subjects have the following additional procedures performed.

PK sub-study—up to 20 subjects (10<120 kg and 10≥120 kg) have blood drawn for PK analysis prior to and following each dose through week 17. For the PK sub-study, up to 20 subjects are included, as follows: Five subjects weighing ≥120 kg receive 12 mg loading dose, followed by 8 mg at each subsequent dose through week 25. Five subjects weighing ≥120 kg receive 16 mg loading dose, followed by 8 mg at each subsequent dose through week 25. Five subjects weighing <120 kg receive 12 mg loading dose, followed by 8 mg at each subsequent dose through week 25. Five subjects weighing <120 kg receive 16 mg loading dose, followed by 8 mg at each subsequent dose through week 25.

Joint Imaging sub-study—up to 20 subjects weighing <120 kg have DECT and DCE-MRI performed at Screening and at Week 17 or Early Termination. For the Joint Imaging sub-study, 20 subjects weighing <120 kg are included.

Example 4—Inclusion Criteria

Subjects to be included in the study are:
1. Adult (age ≥18 years) men and women of non-childbearing potential, with chronic gout refractory to conventional therapy, defined as subjects who failed to achieve a sustained SUA of <6 mg/dL and whose signs and symptoms are inadequately controlled with xanthine oxidase inhibitors at a medically appropriate dose or for whom these drugs are contraindicated.
2. Hyperuricemic—Screening visit SUA must be >6 mg/dL
3. On gout flare prophylactic regimen for 7 days prior to the first dose.
4. Willing and able to give informed consent and adhere to visit/protocol schedules (informed consent must be given before the first study procedure is performed)

Example 5—Exclusion Criteria

Subjects are to be excluded from the study if any of the following apply:
1. Glucose-6-phosphate dehydrogenase (G6PD) deficiency (confirmed at Screening visit)
2. Non-compensated congestive heart failure, uncontrolled arrhythmia, treatment for acute coronary syndrome (ACS) (myocardial infarction or unstable angina) or hospitalization for congestive heart failure within 3 months of screening or uncontrolled blood pressure (>160/100 mm Hg) at baseline (Screening and pre-dose at Week 1 visit)
3. Women of childbearing potential defined as:
    Pre- or perimenopausal (<24 months of natural [spontaneous] amenorrhea).
    <6 weeks after surgical bilateral oophorectomy with or without hysterectomy
4. Prior treatment with pegloticase or another recombinant uricase
5. Prior treatment or concomitant therapy with a polyethylene glycol (PEG) conjugated drug
6. Known allergy to PEG products or history of anaphylactic reaction to a recombinant protein or porcine product
7. Concurrent treatment with urate-lowering agents (ULAs), such as allopurinol and febuxostat. Subjects treated with these medications must discontinue treatment 7 days prior to the first dose of study drug
8. Recipient of an investigational drug within 4 weeks (or 5 half-lives) prior to study drug administration or plans to take an investigational agent during the study
9. Current liver disease as determined by alanine transaminase (ALT) or aspartate transaminase (AST) levels >3 times upper limit of normal (ULN)
10. History of malignancy within 5 years other than basal cell skin cancer or carcinoma in situ of the cervix
11. Has any other medical or psychological condition which, in the opinion of the Investigator, might create undue risk to the subject or interfere with the subject's ability to comply with the protocol requirements, or to complete the study
12. Solid organ transplant recipients
13. Uncontrolled hyperglycemia with a serum glucose value >240 mg/dL at screening
14. Currently on dialysis Additional Exclusion Criteria for Joint Imaging Sub-Study Only:
15. Contraindication to receiving a macrocyclic gadolinium-based contrast agent (GBCA) or >2 previous lifetime exposures to a macrocyclic GBCA—subjects who meet this exclusion criteria will be given the option to have an MRI without contrast agent
16. Implanted pacemaker, certain older intracranial aneurysm clips, cochlear implants, certain prosthetic devices, implanted drug infusion pumps, neurostimulators, bone-growth stimulators, certain intrauterine contraceptive devices, or any other type of iron-based metal implants.
17. Any internal metallic objects such as bullets or shrapnel, as well as most surgical clips, pins, plates, screws, metal sutures, or wire mesh.

Additional Exclusion Criteria for Pegloticase and AZA Arm:
18. Any active serious bacterial infection (2 weeks prior to screening) requiring antibiotic treatment
19. Severe chronic or recurrent bacterial infections, such as recurrent pneumonia, chronic bronchiectasis
20. Current immunocompromised condition, including current or chronic treatment with systemic immunosuppressive agents (e.g., prednisone or equivalent dose >10 mg/day)
21. At risk for tuberculosis. Specifically, subjects with: a) current clinical, radiographic, or laboratory evidence of active or latent tuberculosis; b) a history of active tuberculosis within the last 1 year even if it was treated; c) a history of active tuberculosis >1 year ago unless there is documentation that the prior anti-tuberculosis treatment was appropriate in duration and type
22. Known history of hepatitis B surface antigen-positivity or hepatitis B DNA positivity
23. Known history of hepatitis C RNA-positivity
24. Known history of human immunodeficiency virus positivity
25. Severe chronic renal impairment (glomerular filtration rate <25 mL/min/1.73 m2)
26. AZA treatment is contraindicated or considered inappropriate
27. Subject has a homozygous thiopurine methyltransferase (TPMT) variant genotype
28. Diagnosis of osteomyelitis
29. Known hypoxanthine-guanine phosphoribosyl-transferase deficiency, such as Lesch-Nyhan and Kelley-Seegmiller syndrome
30. Concurrent use of a xanthine oxidase inhibitor
31. Abnormal hematology results:
    Hemoglobin <10 g/dL
    Platelets <100,000 cells/mm3
    White blood cell count <2000 cells/mm3
    Absolute lymphocyte count <600 cells/mm3
    Absolute neutrophil count <800 cells/mm3
32. Abnormal liver function tests:
    Alkaline phosphatase >290 IU/L
    Alanine aminotransferase >140 IU/L for males, >113 IU/L for females
    Aspartate aminotransferase >100 IU/L Example 6—Selection of Population The subject population in this study will be hyperuricemic (SUA>6 mg/dL) adult men and women (age ≥18) diagnosed with chronic gout refractory to conventional therapy, defined as subjects who have failed to normalize SUA and whose signs and symptoms are inadequately controlled with xanthine oxidase inhibitors at the maximum medically appropriate dose, or for whom these drugs are contraindicated (e.g., develop allergic reactions/severe hypersensitivity syndrome).

The study will plan to enroll up to a total of 177 subjects, 37 of whom must weigh ≥120 kg at screening, and 40 subjects who will receive pegloticase and AZA immunosuppressive therapy.

Subjects who discontinue the study prematurely for reasons other than not responding to pegloticase (Non-Responder—see below) will be replaced. The study will be conducted at up to 22 centers in the US. Enrollment is anticipated to last up to 3 years.

Example 7—Pegloticase Test Drug Product

KXX (pegloticase) is a PEGylated uric acid specific enzyme indicated for the treatment of chronic gout in adult patients refractory to conventional therapy. Gout refractory to conventional therapy occurs in patients who have failed to normalize serum uric acid and whose signs and symptoms are inadequately controlled with xanthine oxidase inhibitors at the maximum medically appropriate dose or for whom these drugs are contraindicated.

Pegloticase is a clear, colorless, sterile solution in phosphate-buffered saline intended for IV infusion after dilution, will be supplied by Horizon as KXX. KXX is commercially available in the US in a single-use, 2 mL glass vial with a Teflon coated (latexfree) rubber injection stopper. Each mL of KXX contains 8 mg of uricase protein conjugated to 24 mg of 10 kDa monomethoxypoly (ethylene glycol) (mPEG). Excipients include disodium hydrogen phosphate dihydrate, sodium chloride, sodium dihydrogen phosphate dehydrate, and water for injection. KXX will be provided to sites as commercially packaged.

KXX is supplied as a clear, colorless, sterile solution in phosphate buffered saline intended for intravenous infusion after dilution. KXX is supplied in a single-use 2 mL glass vial with a Teflon® coated (latex-free) rubber injection stopper to deliver KXX as 8 mg of uricase protein in 1 mL volume. Before preparation for use, pegloticase should be stored in the carton, maintained under refrigeration between 2° C. and 8° C. (36° F. and 46° F.), protected from light, and should not be shaken or frozen.

In accordance with good pharmacy practice, gloves should be worn during preparation of the dose.

Vials should be visually inspected for particulate matter and discoloration before administration, whenever solution and container permit. Vials should not be used if either is present. Using appropriate aseptic technique, the required volume of pegloticase should be withdrawn from the vial into a sterile syringe, according to the table below. Two vials of pegloticase will be necessary to ensure the full dose volume for 12 mg and 16 mg doses. Any unused portion of product remaining in the vial(s) should be discarded. Syringe contents should be injected into a single 250 mL bag of 0.45% or 0.9% Sodium Chloride Injection, United States Pharmacopeia (USP) for IV infusion and should not be mixed or diluted with other drugs. The infusion bag containing the dilute pegloticase solution should be inverted a number of times to ensure thorough mixing, but should not be shaken. For a dose of 8 mg pegloticase, the volume is 1.0 mL; for a dose of 12 mg, the volume is 1.5 mL; and for a dose of 16 mg, the volume is 2.0 mL.

Pegloticase-diluted in infusion bags is stable for 4 hours at 2° C. to 8° C. (36° F. to 46° F.) and at room temperature (20° C. to 25° C., 68° F. to 77° F.); however, it is recommended that the diluted solution be stored under refrigeration, not frozen, protected from light, and used within 4 hours of dilution. Before administration, the diluted solution of pegloticase should be allowed to reach room temperature.

Pegloticase in a vial or in an IV infusion fluid should never be subjected to artificial heating.

Example 8—Administration of Pegloticase

Subjects should NOT be fasting on the day of infusion; they should be encouraged to have a snack or normal meal 1 hour before or immediately after the infusion. There are no fluid restrictions.

Pegloticase will be administered as an admixture of 8, 12, or 16 mg in 250 mL of 0.45% or 0.9% Sodium Chloride Injection, USP for IV infusion over a target infusion time of 120 minutes by gravity feed or infusion pump. It should not be administered as an IV push or bolus. Standardized IR prophylaxis consisting of pre-treatment with antihistamines and corticosteroids will accompany each infusion. The drug name, dose, and timing of these prophylactic medications will be recorded in the subject medical record and in the electronic case report/record form (eCRF). In a patent IV site, using tubing with no in-line filter, infuse the drug preparation over approximately 120 minutes (within ±15 minutes) while the subject is under close observation for any signs of distress. The bag and tubing do not need to be protected from ambient light during the infusion period. At the end of the infusion, the IV line should be flushed with 10 mL of normal saline to assure the full dose is administered.

Administration of drug is to be immediately discontinued if respiratory distress, agitation, chest or back pain, urticaria, or another clinically significant event occurs during infusion.

As a precaution, emergency equipment must be readily available to treat a possible hypersensitivity reaction, and must include drugs that would be used to treat an anaphylactic reaction. Personnel fully trained in advanced cardiopulmonary resuscitation and in the use of the emergency equipment must be readily available during and for 1 hour after the infusion. In order to ensure subjects do not experience IRs, subjects are observed for 1 hour post-infusion.

Dosage Forms and Strengths

KXX is a clear, colorless, sterile 8 mg/mL solution of pegloticase in a 2 mL single use vial, expressed as amounts of uricase protein. KXX must be diluted prior to use.

Dosage

The recommended dose and regimen of KXX for adult patients is 8 mg (uricase protein) given as an intravenous infusion every two weeks. The optimal treatment duration with KXX has not been established.

Preparation

Visually inspect KXX for particulate matter and discoloration before administration, whenever solution and container permit. Do not use vials if either is present. Use appropriate aseptic technique. Withdraw 1 mL of KXX from the vial into a sterile syringe. Discard any unused portion of product remaining in the 2-mL vial. Inject into a single 250 mL bag of 0.9% Sodium Chloride Injection, USP or 0.45% Sodium Chloride Injection, USP for intravenous infusion. Do not mix or dilute with other drugs.

Invert the infusion bag containing the dilute KXX solution a number of times to ensure thorough mixing. Do not shake.

KXX diluted in infusion bags is stable for 4 hours at 2° to 8° C. (36° to 46° F.) and at room temperature (20° to 25° C., 68° to 77° F.). However, it is recommended that diluted solutions be stored under refrigeration, not frozen, protected from light, and used within 4 hours of dilution. Before administration, allow the diluted solution of KXX to reach room temperature. KXX in a vial or in an intravenous infusion fluid should never be subjected to artificial heating (e.g., hot water, microwave).

Administration

KXX is not administered as an intravenous push or bolus. It is recommended that before starting KXX patients discontinue oral urate lowering medications and not institute therapy with oral urate-lowering agents while patients are on KXX therapy.

Monitoring Therapy: The risk of anaphylaxis and infusion reactions is higher in patients who have lost therapeutic response. Monitor serum uric acid levels prior to infusions and consider discontinuing treatment if levels increase to above 6 mg/dL, particularly when 2 consecutive levels above 6 mg/dL are observed.

The KXX admixture should only be administered by intravenous infusion over no less than 120 minutes via gravity feed, syringe-type pump, or infusion pump.

Patients should receive pre-infusion medications (e.g. antihistamines, corticosteroids), to minimize the risk of anaphylaxis and infusion reactions. Administer KXX in a healthcare setting and by healthcare providers prepared to manage anaphylaxis and infusion reactions, and observe patients for an appropriate period of time after administration.

If an infusion reaction occurs during the administration of KXX, the infusion may be slowed, or stopped and restarted at a slower rate, at the discretion of the physician. Since infusion reactions can occur after completion of infusion, observation of patients for approximately an hour post-infusion should be considered.

Example 9—Azathioprine

AZA is a purine analogue. AZA is available in tablet form for oral administration. Each scored tablet contains 50 mg AZA and the inactive ingredients lactose, magnesium stearate, potato starch, povidone, and stearic acid.

AZA will be provided by AMPEL BioSolution as generic, commercially packaged: 50 mg scored tablets; in bottles of 100. Bottles of AZA should be stored at 15° C. to 25° C. (59° F. to 77° F.) in a dry place and protected from light.

Subjects will take AZA starting 2 weeks prior to dosing with pegloticase (run-in period). Subjects will take 1.25 mg/kg orally daily during Week −2 of the run-in period. From Week −1 of the Run-In Phase through Week 25 of the study, subjects will take 2.5 mg/kg orally daily of AZA. Dose should be rounded to the nearest 25 mg.

Subjects who have heterozygous TPMT variant genotype will be restricted to a dose of 1.25 mg/kg during the 2 week run-in period and through Weeks 1 to Week 25 of the study.

Investigational clinical supplies must be received by a designated person at the study site, handled and stored safely and properly, and kept in a secured location to which only the Investigator and designated assistants have access. Clinical supplies are to be dispensed only in accordance with the protocol. The Investigator is responsible for keeping accurate records of the clinical supplies received from Horizon or AMPEL BioSolutions, the amount dispensed for each subject, and the amount remaining at the conclusion of the study.

Mark the label of any vials of pegloticase that are not to be used with a large X, and document the reason for rejecting them on the drug accountability log. Used vials should be kept until a study monitor has verified drug accountability, and then disposed of or destroyed properly.

Example 10—Pegloticase Pretreatment Medications

All subjects will receive pre-treatment prophylaxis consisting of at least an antihistamine and corticosteroid before each infusion of pegloticase. The name, route, and date of administration of each prophylactic medication will be recorded in the medical record and in the eCRF. The Sponsor will provide these medications to each site.

The night before infusion, subjects took fexofenadine, 60 mg (PO). The morning of the infusion, subjects took fexofenadine, 60 mg (PO) and acetaminophen, 1000 mg (PO). Following arrival at the infusion clinic, subjects received an abbreviated physical examination, which included a dermatological exam, noting any rashes, and the chest is examined, noting breath sounds and vital signs. An IV is started to administered hydrocortisone, 200 mg. Drug infusion is then initiated.

Example 11—Management of Infusion Reactions

Subjects must be monitored closely for signs and symptoms of IRs. In the event of an IR, the infusion should be slowed, or stopped and restarted at a slower rate at the discretion of the Investigator. If a severe IR occurs, discontinue infusion and institute treatment as needed.

In addition, if a subject experienced an IR, the following procedures will be undertaken:
  A physical examination to capture medically relevant details, including but not limited to, a thorough dermatologic examination for detection of erythema, urticaria (hives), or peri-oral or lingual edema; a chest examination for breath sounds, stridor or wheezing; and a cardiac examination with attention to irregular heartbeat.
  Vital signs (sitting or supine blood pressure, heart rate, respiratory rate, and body temperature) will be captured at least every 30 minutes until the resolution or stabilization of the AE.
  The Investigator may administer any medically indicated pharmacologic agent or procedure intended to relieve symptoms (CAUTION: no other drugs can be mixed in the pegloticase infusion bag). Signs and symptoms of the AE and drugs given for treatment are to be recorded in the medical record and in the eCRF.

If in the Investigator's opinion, the subject is experiencing an anaphylactic reaction, treatment with pegloticase should be immediately and permanently discontinued. Any incidence of anaphylaxis must be reported as an SAE. The NIAID/FAAN clinical criteria for diagnosing anaphylaxis are used in this study After the first experience of an IR that does not meet the criteria of anaphylaxis, the Investigator may elect to initiate the next infusion at a slower rate. Additionally, the Investigator may choose to prescribe 20 mg prednisone the morning of the next infusion. All changes to infusion rate or dilution, and drugs given for prophylaxis or treatment, are to be recorded in the medical record and in the eCRF.

Example 12—Prophylaxis for Gout Flares

Subjects not already on a prophylactic regimen of colchicine or non-steroidal anti-inflammatory drug (NSAID) to prevent gout flares should be placed on one of these agents at the time of study entry, unless medically contraindicated. Subjects must be on the prophylactic regimen for 7 days prior to the first infusion.

Example 13—Oral Urate-Lowering Therapy

Because of the possibility that concomitant use of oral urate-lowering therapy (xanthine oxidase inhibitors) and pegloticase may potentially blunt the rise of serum uric acid levels, pharmaceutical agents specifically approved for lowering SUA (e.g., allopurinol or febuxostat) should not be used in conjunction with pegloticase. Xanthine oxidase inhibitors have a drug-drug interaction with AZA, inhibiting one of the AZA metabolic inactivation pathways, increasing the risk of leukopenia. For subjects receiving pegloticase and AZA, it is important that oral urate-lowering therapies be discontinued. After discontinuation of pegloticase and AZA, another urate-lowering drug may be instituted at any time.

Example 14—Main Study Loading Doses

Analysis of data from prior pegloticase randomized clinical trials have suggested that subjects weighing ≥120 kg may respond to pegloticase differently. In the ≥120 kg group, the initial serum peak of pegloticase (Cmax) is lower, the impact on serum urate is less, and they have a greater tendency to become non-responders. It has been estimated that the single fixed non-weight based dosing regimen may significantly underdose people weighing ≥120 kg. Based on these considerations, it is proposed to carefully increase the loading dose of pegloticase in persons weighing ≥120 kg. Three cohorts of subjects weighing ≥120 kg will be sequentially enrolled to receive loading doses of pegloticase at 8, 12, and 16 mg, to reflect comparable weight-based dosages in subjects weighing <120 kg. Three subjects will receive an 8 mg loading dose per original protocol. Subsequently, 5 subjects will receive a 12 mg loading dose and if no untoward effects are observed, a third cohort of 5 subjects will receive a 16 mg loading dose. Trough levels of pegloticase will be determined throughout the study to document the impact of dose escalation on serum pegloticase levels, SUA, and likelihood of becoming a treatment responder.

Example 15—Laboratory Assessments

Vital Signs—Temperature, heart rate, blood pressure and respiratory rate. Except for temperature, vital signs will be measured following a 5-minute rest in a semi-recumbent position.
Laboratory Assessments
  Serum chemistries—alanine transaminase (ALT), aspartate transaminase (AST), alkaline phosphatase, total bilirubin, lactate dehydrogenase (LDH), creatinine, uric acid, glucose, total cholesterol, sodium, potassium, calcium, chloride, total protein, blood urea nitrogen (BUN), and estimated glomerular filtration rate (eGFR [AZA arm only])
  Liver function tests—ALT, AST, and alkaline phosphatase
  Hematology—hemoglobin concentration, hematocrit, erythrocyte, platelet and white blood count (WBC) and differential
  Serum uric acid (SUA)
  Serum G6PD
  Whole blood for TPMT activity (AZA arm only)

Serum for high sensitivity C-reactive protein (hs-CRP)
Serum for future analysis of antibodies directed against pegloticase (IgG and IgM) and PEG
Serum for trough pegloticase levels
Whole blood for trough AZA metabolite levels
Modified medical history—presence or absence of the following diagnoses: hypertension, dyslipidaemia, diabetes mellitus, coronary artery disease, cardiac failure
Complete physical exam—examination of the following: skin, HEENT, lungs/chest, heart, abdomen, musculoskeletal, extremities, neurologic, and lymphatic systems
Symptom driven physical exam—focused examination of the subject following medical history
Infusion Reactions
Adverse Events Example 16—Study Procedures—Laboratory Assessments for Sub-Studies PK Sub-Study:
Serum for pegloticase levels.
Joint Imaging Sub-Study:
Subjects participating in the Joint Imaging Sub-study who have a contraindication to macrocyclic GBCA or >2 previous lifetime exposures to a macrocyclic GBCA will have an MRI without contrast.
DECT will be obtained at baseline on the hands/wrists, knees, ankles/feet, and the investigator will identify the primary area of major urate deposition. Then DCE-MRI sequences will be obtained on this primary area (a single area-hand/wrist, knee, or ankle/foot) to assess inflammation of urate deposits. The same areas will be then assessed at week 17 or Early Termination. The imaging will be and performed by study-specific pre-qualified and trained radiology staff. All procedures and processes for the acquisition of the images are specified in the study-specific Imaging Acquisition Charter.

Example 17—Main Study Procedures

Screening (Day −21 Through Day −3)
Subjects will be screened to assess eligibility criteria within −21 through −3 days prior to the Week 1 visit (first dose). The following assessments and procedures will be performed:
Written informed consent, including sub-study consent(s) as applicable
Medical history, including medication history
Demographics
Concomitant medications review
Complete physical exam, including vital signs, height, and weight
Blood collection for:
  Chemistries—subjects must be fasting
  Hematology
  SUA
  G6PD
  hs-CRP
Schedule Week 1 visit, ensure subject is taking gout flare prophylaxis, and provide pre-treatment prophylaxis instructions.
All screened subjects must be entered into EDC at the time of screening to obtain a subject ID. Additionally, please immediately notify the study Project Manager of all screened subjects weighing ≥120 kg or participating in the PK sub-study, to ensure proper assignment to loading dose cohorts.
Day 1/Week 1/Dose 1
Eligible subjects will come to the clinic on Week 1. The following assessments are to be completed prior to the start of the pegloticase infusion:
Review of Eligibility Criteria
Assess and record concomitant medications
Symptom driven physical exam
Vital signs, following a 5-minute rest in a semi-recumbent position
Blood collection for:
  SUA
  Anti-pegloticase antibodies
  Anti-PEG antibodies
  Trough pegloticase level
Following the above assessments, the infusion will begin as described herein. Subjects will be monitored for IRs and AEs throughout the infusion and for 1 hour following the infusion.
Weeks 2 and 3 (±1 Day), Weeks 5, 7, 9, 11, 13, 15, 17, 19, 21, 23, and 25 (±2 Days)
The subject must have blood drawn for SUA at a local lab within 24 hours prior to dosing. If the SUA is >6 mg/dL, the subject may not be dosed and the SUA should be repeated by the central lab. If the SUA is >6 mg/dL by the central lab, the subject will be declared a treatment failure and the subject must be withdrawn from the study. Samples that result in discordant results between local and central laboratories will be evaluated and discussed with the PI and the sponsor medical monitor on a case by case basis as to whether the subject should continue on study drug or discontinue dosing.
The following assessments are to be completed prior to the start of the pegloticase infusion:
Symptom driven physical exam
Vital signs
Blood collection for:
  SUA
  Anti-pegloticase antibodies
  Anti-PEG antibodies
  Trough pegloticase level
  hs-CRP
Assessment of AEs
Assessment of concomitant medications
Following the above assessments, the infusion will begin as described herein. Subjects will be monitored for IRs and AEs throughout the infusion and for 1 hour following the infusion.
Week 25 (±2 Days) or Early Withdrawal
The subject must have blood drawn for SUA at a local lab within 24 hours prior to dosing. If the SUA is >6 mg/dL, the subject may not be dosed and the SUA should be repeated by the central lab.
The following assessments are to be completed prior to the start of the pegloticase infusion or at the time of early withdrawal from the study:
Symptom driven physical exam
Vital signs
Blood collection for:
  Chemistries—subjects must be fasting
  Hematology
  SUA
  Anti-pegloticase antibodies Anti-PEG antibodies
Trough pegloticase level
hs-CRP
Assessment of AEs
Assessment of concomitant medications Following the above assessments and if the subject is not withdrawn from the study, the infusion will begin as described herein. Subjects will be monitored for IRs and AEs throughout the infusion and for 1 hour following the infusion.

Example 18—PK Sub-Study Procedures

Following the Screening Visit, eligible subjects participating in the PK Sub-Study will have all procedures listed herein, in addition to the procedures listed in this section. Note that PK sample collection stops after Week 17, however subjects should continue the schedule through Week 25.

Day 1/Week 1/Dose 1, Week 2/Dose 2, and Week 3/Dose 3
Serum for pegloticase levels will be obtained immediately prior to dosing and then at 2, 4, 24 (±4), 48 (±4), and 96 (+24) hours following the end of the infusion.

Week 5/Dose 4, Week 7/Dose 5, Week 9/Dose 6, Week 11/Dose 7, Week 13/Dose 8, Week 15/Dose 9
Serum for pegloticase levels will be obtained immediately prior to dosing and then at 2 and 24 (±4) hours following the end of the infusion.

Week 17/Dose 10
Serum for pegloticase levels will be obtained immediately prior to dosing and then at 2, 4, 24 (±4), 48 (±4), 96 (+24), and 168 (±24) hours following the end of the infusion.

Example 19—Joint Imaging Sub-Study Procedures

Following the Screening Visit, eligible subjects participating in the Joint Imaging Sub-Study will have the all the procedures described herein, in addition to the following procedures performed prior to Week 1/Dose 1 and after the Week 17 dose or Early Termination:
DECT of both hands/wrists, knees, and feet/ankles. The investigator will review the images and select the most involved joint for DCE-MRI/MRI imaging.
DCE-MRI or MRI of the most involved joint.

Example 20—Pegloticase and AZA Arm Procedures

Screening (Day −28 Through Day −14)
Subjects will be screened to assess eligibility criteria within −28 through −14 days prior to the Week 1 visit (first dose of pegloticase). The following assessments and procedures will be performed:
Written informed consent, including sub-study consent(s) as applicable
Medical history, including medication history
Demographics
Concomitant medications review
Complete physical exam, including vital signs, height, and weight
Blood collection for:
Chemistries, including eGFR—subjects must be fasting
Hematology
SUA
G6PD
TPMT activity
hs-CRP Schedule Week 1 visit, ensure subject is taking gout flare prophylaxis, and provide pre-treatment prophylaxis instructions
All screened subjects must be entered into EDC at the time of screening to obtain a subject ID.

AZA Run-in Period: Day −14
Eligible subjects will come to the clinic on Day −14 to begin immunosuppressive therapy with AZA. From Day −14 to Day −7, subjects will take AZA 1.25 mg/kg orally each day.

AZA Run-in Period: Day −7
Eligible subjects will come to the clinic on Day −7. The following assessments and procedures will be performed:
Blood collection for:
Liver function tests
Hematology
Trough AZA metabolite level From Day −7 through Day 1, subjects will take AZA 2.5 mg/kg orally each day. Subjects who have heterozygous TPMT variant genotype will remain on 1.25 mg/kg orally each day.

Day 1/Week 1/Dose 1
Eligible subjects will come to the clinic on Week 1. The following assessments and procedures will be performed prior to the start of the pegloticase infusion:
Review of Eligibility Criteria
Assess and record concomitant medications
Symptom driven physical exam
Vital signs, following a 5-minute rest in a semi-recumbent position
Blood collection for:
Liver function tests
Hematology
SUA
hs-CRP
Anti-pegloticase antibodies
Anti-PEG antibodies
Trough pegloticase level
Trough AZA metabolite level Following the above assessments, the infusion will begin as described herein. Subjects will be monitored for IRs and AEs throughout the infusion and for 1 hour following the infusion.

Weeks 3, 5, 7, 9, 11, 13, 15, 17, 19, 21, and 23 (±2 Days)
The subject must have blood drawn for SUA at a local lab within 24 hours prior to dosing. If the SUA is >6 mg/dL, the subject may not be dosed and the SUA should be repeated by the central lab. If the SUA is >6 mg/dL by the central lab, the subject will be declared a treatment failure and the subject must be withdrawn from the study. Samples that result in discordant results between local and central laboratories will be evaluated and discussed with the PI and the sponsor medical monitor on a case by case basis as to whether the subject should continue on study drug or discontinue dosing.

The following assessments are to be completed prior to the start of the pegloticase infusion:
Symptom driven physical exam
Vital signs
Blood collection for:
Liver function tests
Hematology
SUA
hs-CRP
Anti-pegloticase antibodies
Anti-PEG antibodies Trough pegloticase level
Trough AZA metabolite level
Assessment of AEs
Assessment of concomitant medications Following the above assessments, the infusion will begin as described herein. Subjects will be monitored for IRs and AEs throughout the infusion and for 1 hour following the infusion.

Week 25 (±2 Days) or Early Withdrawal

The subject must have blood drawn for SUA at a local lab within 24 hours prior to dosing. If the SUA is >6 mg/dL, the subject may not be dosed and the SUA should be repeated by the central lab.

The following assessments are to be completed prior to the start of the pegloticase infusion or at the time of early withdrawal from the study:
Symptom driven physical exam
Blood collection for:
  Chemistries, including eGFR—subjects must be fasting
  Hematology responsibility of the Investigator or Sub-Investigator(s) to perform periodic assessments of all AEs. Data describing AEs will be entered in the subject's medical record and eCRF. SAEs will be reported to the Sponsor.

Subjects who experience AEs, whether serious or not serious, should receive appropriate treatment and medical supervision as clinically indicated. All AEs must be followed until resolution/stabilization or until a time that is mutually agreed upon between the Medical Monitor and the Investigator.

Severity in accordance with the disclosure was reported according to the following: Grade 1 (Mild)—No interference with daily activity. Grade 2 (Moderate)—Some interference with daily activity but medical intervention not required (e.g., doctor visit and/or medication); over the counter medicine permitted. Grade 3 (Severe)—Prevents daily activity and requires medical intervention (e.g., doctor visit and/or medication). Grade 4 (Potentially Life-threatening)—Emergency room visit or hospitalization. Severity of hematology and liver function tests is reported in accordance with the following.

TABLE 3

Severity Grading for Hematology and Liver Function Tests

| Parameter | Grade 1 Mild | Grade 2 Moderate | Grade 3 Severe | Grade 4 Potentially Life-threatening |
| --- | --- | --- | --- | --- |
| Alkaline Phosphatase, High | 1.25 to <2.5 × ULN | 2.5 to <5.0 × ULN | 5.0 to <10.0 × ULN | ≥10.0 × ULN |
| ALT, High | 1.25 to <2.5 × ULN | 2.5 to <5.0 × ULN | 5.0 to <10.0 × ULN | ≥10.0 × ULN |
| AST, High | 1.25 to <2.5 × ULN | 2.5 to <5.0 × ULN | 5.0 to <10.0 × ULN | ≥10.0 × ULN |
| Hemoglobin, Low (g/dL)-male | 10.0 to 10.9 | 9.0 to <10.0 | 7.0 to <9.0 | <7.0 |
| Hemoglobin, Low (g/dL)-female | 9.5 to 10.4 | 8.5 to <9.5 | 6.5 to <8.5 | <6.5 |
| Platelets, Low ($10^3$ cells/μL) | 100 to 124 | 50 to 100 | 25 to 50 | <25 |
| WBC, Low ($10^3$ cells/μL) | 2.0 to 2.5 | 1.5 to 1.99 | 1.0 to 1.49 | <1.0 |
| Absolute Lymphocyte Count, Low ($10^3$ cells/μL) | 0.600 to <0.650 | 0.500 to <0.600 | 0.350 to <0.500 | <0.350 |
| Absolute Neutrophil Count (ANC), Low ($10^3$ cells/μL) | 0.800 to 1.0 | 0.600 to 0.799 | 0.400 to 0.599 | <0.400 |

SUA
hs-CRP
Anti-pegloticase antibodies
Anti-PEG antibodies
Trough pegloticase level
Trough AZA metabolite level
Assessment of AEs
Assessment of concomitant medications Following the above assessments and if the subject is not withdrawn from the study, the infusion will begin as described herein. Subjects will be monitored for IRs and AEs throughout the infusion and for 1 hour following the infusion.

Example 21—Adverse Events

AEs are reported in a manner consistent with the FDA Guidance for Industry and Investigators, "Safety Reporting Requirements for IND and BA/BE Studies," December 2012 (fda.gov/downloads/Drugs/GuidanceCompliance-RegulatoryInformation/Guidances/UCM227351.pdf).

AEs are reported from the time of the first dose through Week 25 or early withdrawal from the study. It is the Clinical Laboratory Abnormalities—Any clinical laboratory abnormality, except for SUA, deemed clinically significant by the Investigator should be reported as an AE. A clinically significant abnormality is a confirmed abnormality (by repeat test) that is changed sufficiently from Screening/Baseline so that in the judgment of the Investigator a change in management is warranted. This alteration may include: monitoring the laboratory test further, initiating other diagnostic tests or procedures, changing ongoing treatment, or administering new treatment. Whenever possible, the underlying medical diagnosis (e.g., anemia) should be reported as the SAE term. Repeated additional tests and/or other evaluations required to establish the significance and etiology of an abnormal result should be obtained when clinically indicated.

Physical Exam Abnormalities—Any physical exam abnormality deemed clinically significant by the Investigator during the study should be reported as an AE.

Pregnancy—No additional doses should be administered to a subject who becomes pregnant during the conduct of the trial. All remaining safety assessments should be performed. All pregnancies that occur—including female partners of male subjects—during the study must be reported to the Sponsor and followed to conclusion. The outcome of each pregnancy must be reported.

Pregnancy alone is not an AE, nor is an induced elective abortion to terminate a pregnancy without medical reason. However, an induced therapeutic abortion to terminate a pregnancy due to complications or medical reasons must be reported as an SAE. The underlying medical diagnosis for this procedure should be reported as the SAE term. A spontaneous abortion is always considered an SAE.

SAEs must be reported to the Sponsor or designee within 1 business day of becoming aware of the event. If at the time the Investigator submits an initial SAE report the event has not resolved, the Investigator must provide a follow-up report as soon as it resolves (or upon receipt of significant information if the event is still ongoing). All SAEs must be followed until resolution/stabilization or until a time that is mutually agreed upon between the Medical Monitor and the Investigator. Upon checking "serious" on the AE eCRF, a notification will be sent to the Medical Monitor and/or designee. Relevant eCRFs, including the subject's Disease History, Concomitant Medications, and other AEs must also be completed to provide supporting documentation for the SAE.

Any subject experiencing an AE, including clinically significant abnormal laboratory result or physical exam finding, will be monitored at appropriate intervals (e.g., weekly for laboratory abnormalities) until resolution or stabilization, or until a time that is mutually agreed upon between the Medical Monitor and the Investigator After review of the initial SAE report, the Medical Monitor may request additional documentation (e.g., clinic or hospital records, or procedure reports). The Sponsor is responsible for notifying the relevant regulatory authorities of unexpected, serious, drug-related events. It is the Investigator's responsibility to notify the Institutional Review Board (IRB) of all SAEs that occur at his or her site. Investigators will also be notified of all unexpected, serious, drug-related events that occur during the clinical trial. Each site is responsible for notifying its IRB of these additional SAEs.

Example 22—Subject and Study Discontinuation

Screening Failures

Subjects who sign and date the informed consent form but who fail to meet the inclusion and exclusion criteria are defined as screen failures. A screening log, which documents the subject's initials and reason(s) for screen failure, will be maintained for all screen failures. A copy of the log should be retained in the Investigator's study files.
Early Withdrawal from Dosing A subject may be prematurely withdrawn from study dosing for any of the following reasons: (1) SUA by the central lab >6 mg/dL; (2) Safety, including AEs or development of clinically significant laboratory abnormalities. The subject must be followed clinically until the event is resolved or deemed stable. (3) Subject wishes to withdraw consent for reasons other than an AE. (4) Subject non-compliance or unwillingness to comply with the procedures required by the protocol. (5) Investigator discretion. (6) Sponsor request.
Additional Reasons for Subjects Receiving AZA Subject has a Grade 3 or greater hematology or liver function abnormality. The subject must be followed clinically until the event is resolved or deemed stable. Efforts will be made to follow all subjects who discontinue study drug for any reason. Such follow-up will include all relevant evaluations for safety including clinical assessments and collection of laboratory study results as set out in this protocol.
Early Withdrawal from the Study As stated above, any subject who has received at least 1 dose of study drug should be followed for safety. With that said, subjects may be withdrawn from the study for any of the following reasons: (1) Subject has discontinued dosing of study drug(s) and completed early termination assessments. (2) Safety, including AEs or development of clinically significant laboratory abnormalities. The subject must be followed clinically until the event is resolved or deemed stable. (3) Subject wishes to withdraw consent for reasons other than an AE. (4) Subject non-compliance or unwillingness to comply with the procedures required by the protocol. (5) Investigator discretion. (6) Sponsor request.
Study or Site Termination Conditions may arise during the study that could prompt the study to be halted or the study site to be terminated. Conditions that may prompt such considerations include, but are not limited to, the discovery of unexpected, serious, or unacceptable risk to the subjects enrolled in the study; and a decision on the part of Sponsor to suspend, discontinue, or shorten the study.

In addition, study conduct at the study site may warrant termination under conditions that include the following: (1) Failure of Investigator(s) to enroll eligible subjects into the study, (2) Failure of Investigator(s) to comply with International Conference of Harmonisation-Good Clinical Practice (ICH-GCP) guidelines, or FDA guidelines and regulations; (3) Submission of false information from the research facility to the Sponsor, the Clinical Monitor, the FDA, or IRB; (4) Insufficient adherence to protocol requirements, (5) A conflict of interest of the Investigator, his/her institution, or site personnel that would negatively impact the integrity of the clinical trial, or (6) Institution or IRB under investigation for cause by a regulatory agency.

Example 23—Statistics

All data will be analyzed by descriptive statistics and (exploratory) post hoc analyses.
Sample Size The sample size calculations have been completed based on the primary endpoint for the Main Study and a minimum of 20 subjects is required for proof of concept analysis. Because post hoc analysis of the pivotal pegloticase randomized clinical trial determined that the frequency of responsiveness is related to age of the subject, the expansion of the sample size to 40 subjects weighing <120 kg is necessary to provide sufficient subjects in each age band to provide interpretable results.
Analysis Conventions The statistical analysis will be coordinated by the responsible biostatistician. The Statistical Analysis Plan (SAP) will provide additional details on the planned statistical analysis. The SAP will be finalized before the database is locked and any deviations from the SAP will be described in the clinical study report.

Data will be summarized with respect to baseline demographic and screening characteristics, efficacy observations and measurements, safety observations and measurements, and pharmacodynamics (PD) measurements. Imputation will be done for the primary endpoint in the modified intent-to-treat (mITT) population under the assumption that any subjects who withdrew before dose 7 will be considered non-responders. Imputation will be done for secondary efficacy endpoints as appropriate using last observation carried forward (LOCF) or non-responder imputation assumptions. Data will not be imputed for the safety analyses conducted in the safety population.

Descriptive statistics (number of subjects, mean, standard deviation [SD], minimum, median, and maximum) will primarily be used to summarize continuous variables. Where appropriate, continuous variables may also be analyzed using the t-test and/or analysis of variance/covariance (ANOVA/ANCOVA). Descriptive statistics and comparison between groups for categorical variables will primarily consist of frequency and percentage.

Analysis Populations

The mITT Population includes those subjects who received at least 1 dose of Test Product and have at least 1 post-baseline SUA measurement. The mITT Population will be used for all efficacy analyses. The Safety Population includes all subjects who have received at least 1 dose of the Test Product.

Demographic Data and Baseline Characteristics

Screening demographics (age, race/ethnicity, and sex) and other screening characteristics (screening gout disease characteristics, weight, and screening co-morbidities) will be summarized in the mITT Population using standard descriptive statistics (N, mean, SD, 95% CI, median, minimum and maximum). All categorical data will be presented using absolute and relative frequency counts and percentages. Demographic variables such as age, race/ethnicity, sex, and other screening categorical parameters will also be analyzed using Fisher's Exact Test. Continuous type parameters will be analyzed using the t-test and analysis of variance (ANOVA) as appropriate.

Exposure and Compliance

Summary statistics (N, mean, SD, 95% CI, median, minimum, maximum) for exposure to pegloticase will include the duration of exposure and the total number of infusions per subject.

Efficacy

The primary efficacy modified Intent-To-Treat (mITT) analysis will examine responder rates for subjects receiving the tolerizing dose regimen (Week 17) and for subjects receiving pegloticase and AZA immunosuppressive therapy (Week 25). Descriptive statistics for treatment differences between the study treatment groups and the standard dose regimen group from previously reported randomized controlled trials will be constructed and imputation will be done for the primary endpoint in the mITT population under the assumption that any subjects who withdrew before Week 11 will be considered as non-responders.

Subjects will be classified as subjects who respond (Responder) and subjects who do not respond (Non-Responder), according to the following criteria:

Responder:
1. The subject must receive a minimum 7 pegloticase doses and complete the first 11 weeks of the study
2. The last 3 consecutive levels of SUA must be <6 mg/dL
   a. at Week 17 or Week 25 (AZA arm); or
   b. at the last on pegloticase visits before the subject discontinued from the study.

If a subject discontinues from the study for a reason unrelated to a rise in SUA >6 mg/dL or an AE other than gout flares, the subject may still be considered a responder as long as the last 3 consecutive SUA levels while on pegloticase are <6 mg/dL prior to discontinuing pegloticase.

Non-Responder:
1. Two consecutive readings of SUA >6 mg/dL at any time while on pegloticase during the trial; or
2. The subject does not complete at least the first 11 weeks (and a minimum of 7 doses) of pegloticase.

Additionally, SUA normalization (mean SUA±SEM) over time in the study will be examined and results presented separately for subjects who respond and subjects who do not respond.

Secondary efficacy analyses will be conducted to compare treatment specific differences in change in SUA from baseline (defined as Screening visit) to Week 17 or Week 25 (AZA arm), (last observation carried forward [LOCF] imputation), the proportion of subjects with SUA<5 mg/dL at Week 17 or Week 25 (AZA arm), (LOCF imputation), and proportion of subjects with SUA<2 mg/dL at Week 17 or Week 25 (AZA arm), (LOCF imputation).

Exploratory:

For subjects weighing ≥120 kg, the primary analysis methods (Responder and Non-Responder) will be performed and compared across loading dose groups. Infusion reactions will also be compared across loading dose groups. Response rates and infusion reaction rates will be compared across subjects from all weight and treatment groups.

Pegloticase trough levels will be compared across all weight and treatment groups. AZA trough levels will be compared across subjects receiving pegloticase and AZA.

Descriptive statistics of the uricase serum concentrations and PK parameters will be reported for each of the 20 PK subjects, by weight group and loading dose (12 or 16 mg).

The following measures will be reported for the 20 subjects undergoing joint imaging studies: change from baseline in urate deposition volume as imaged with DECT, and change from baseline in inflammatory volume as imaged with DCE-MRI and MRI.

Safety:

Safety analyses will be performed on all subjects who received at least 1 dose of study drug (Safety Population). Safety will be assessed from Study Day 1 through Week 25 and assessments will include an examination of IR rates and anaphylaxis, the frequency and severity of gout flares, AEs and SAEs, the frequency of early terminations due to AEs, and data from other tests and/or examinations (vital signs and clinical laboratory tests).

Infusion Reactions and Anaphylaxis

The frequency of IRs and the percentage of IRs meeting criteria of anaphylaxis will be summarized. IR rates will be compared across subjects from both weight groups.

Adverse Events—Non-Infusion Reactions

AEs will be coded using the Medical Dictionary for Regulatory Affairs (MedDRA) and summarized by dose for frequency, severity and AEs leading to early termination. No formal statistical testing will be done.

Clinically significant physical examination and clinical laboratory abnormalities will be reported as AEs, and summarized as described above.

Laboratory Evaluations

Quantitative data (e.g. clinical lab results) will be summarized by mean, median, SD, and range. Laboratory data will be summarized by presenting shift tables using screening to most extreme post-screening value, change from screening values and flagging of notable values.

Vital Signs

Vital signs will be summarized by treatment group using raw data and change from Baseline values (means, medians, SD, ranges).

Concomitant Medications

Concomitant medications will be categorized by World Health Organization (WHO) classification for therapeutic class and drug name and summarized by number and percentage of subjects per dosing group.

Example 24—Anaphylaxis

During pre-marketing controlled clinical trials, anaphylaxis was reported with a frequency of 6.5% of patients treated with KXX every 2 weeks, compared to none with placebo.

Manifestations included wheezing, peri-oral or lingual edema, or hemodynamic instability, with or without rash or urticaria. Cases occurred in patients being pre-treated with one or more doses of an oral antihistamine, an intravenous corticosteroid and/or acetaminophen. This pre-treatment may have blunted or obscured symptoms or signs of anaphylaxis and therefore the reported frequency may be an underestimate. KXX should be administered in a healthcare setting by healthcare providers prepared to manage anaphylaxis. Patients should be pre-treated with antihistamines and corticosteroids. Anaphylaxis may occur with any infusion, including a first infusion, and generally manifests within 2 hours of the infusion. However, delayed type hypersensitivity reactions have also been reported. Patients should be closely monitored for an appropriate period of time for anaphylaxis after administration of KXX. Patients should be informed of the symptoms and signs of anaphylaxis and instructed to seek immediate medical care should anaphylaxis occur after discharge from the healthcare setting.

The risk of anaphylaxis is higher in patients whose uric acid level increases to above 6 mg/dL, particularly when 2 consecutive levels above 6 mg/dL are observed. Monitor serum uric acid levels prior to infusions and consider discontinuing treatment if levels increase to above 6 mg/dL. Because of the possibility that concomitant use of oral urate-lowering therapy and KXX may potentially blunt the rise of serum uric acid levels, it is recommended that before starting KXX patients discontinue oral urate-lowering medications and not institute therapy with oral urate-lowering agents while taking KXX.

Example 25—Infusion Reactions

During pre-marketing controlled clinical trials, infusion reactions were reported in 26% of patients treated with KXX 8 mg every 2 weeks, and 41% of patients treated with KXX 8 mg every 4 weeks, compared to 5% of patients treated with placebo. These infusion reactions occurred in patients being pre-treated with an oral antihistamine, intravenous corticosteroid and/or acetaminophen. This pre-treatment may have blunted or obscured symptoms or signs of infusion reactions and therefore the reported frequency may be an underestimate.

KXX should be administered in a healthcare setting by healthcare providers prepared to manage infusion reactions. Patients should be pre-treated with antihistamines and corticosteroids. KXX should be infused slowly over no less than 120 minutes. In the event of an infusion reaction, the infusion should be slowed, or stopped and restarted at a slower rate.

The risk of infusion reaction is higher in patients whose uric acid level increases to above 6 mg/dL, particularly when 2 consecutive levels above 6 mg/dL are observed. Monitor serum uric acid levels prior to infusions and consider discontinuing treatment if levels increase to above 6 mg/dL. Because of the possibility that concomitant use of oral urate-lowering therapy and KXX may potentially blunt the rise of serum uric acid levels, it is recommended that before starting KXX patients discontinue oral urate-lowering medications and not institute therapy with oral urate-lowering agents while taking KXX.

G6PD Deficiency Associated Hemolysis and Methemoglobinemia

Life threatening hemolytic reactions and methemoglobinemia have been reported with KXX in patients with glucose-6-phosphate dehydrogenase (G6PD) deficiency.

Because of the risk of hemolysis and methemoglobinemia, do not administer KXX to patients with G6PD deficiency. Screen patients at risk for G6PD deficiency prior to starting KXX. For example, patients of African, Mediterranean (including Southern European and Middle Eastern), and Southern Asian ancestry are at increased risk for G6PD deficiency.

Gout Flares

Gout flares may occur after initiation of KXX. An increase in gout flares is frequently observed upon initiation of anti-hyperuricemic therapy, due to changing serum uric acid levels resulting in mobilization of urate from tissue deposits.

Gout flare prophylaxis with a non-steroidal anti-inflammatory drug (NSAID) or colchicine is recommended starting at least 1 week before initiation of KXX therapy and lasting at least 6 months, unless medically contraindicated or not tolerated. KXX does not need to be discontinued because of a gout flare. The gout flare should be managed concurrently as appropriate for the individual patient.

Congestive Heart Failure

KXX has not been formally studied in patients with congestive heart failure, but some patients in the clinical trials experienced exacerbation. Exercise caution when using KXX in patients who have congestive heart failure and monitor patients closely following infusion.

Re-Treatment with KXX

No controlled trial data are available on the safety and efficacy of re-treatment with KXX after stopping treatment for longer than 4 weeks. Due to the immunogenicity of KXX, patients receiving re-treatment may be at increased risk of anaphylaxis and infusion reactions. Therefore, patients receiving re-treatment after a drug-free interval should be monitored carefully.

Example 26—Adverse Reactions

The most commonly reported serious adverse reactions from pre-marketing controlled clinical trials were anaphylaxis, which occurred at a frequency of 6.5% in patients treated with KXX 8 mg every 2 weeks, compared to none with placebo; infusion reactions, which occurred at a frequency of 26% in patients treated with KXX 8 mg every 2 weeks, compared to 5% treated with placebo; and gout flares, which were more common during the first 3 months of treatment with KXX compared with placebo. All patients in pre-marketing controlled clinical trials were pre-treated with an oral antihistamine, intravenous corticosteroid and/or acetaminophen to prevent anaphylaxis and infusion reaction.

Patients also received non-steroidal anti-inflammatory drugs or colchicine, or both, for at least 7 days as gout flare prophylaxis before beginning KXX treatment.

Clinical Trials Experience

The data described below reflect exposure to KXX in patients with chronic gout refractory to conventional therapy in two replicate randomized, placebo-controlled, double-blind 6-month clinical trials: 85 patients were treated with KXX 8 mg every 2 weeks; 84 patients were treated with KXX 8 mg every 4 weeks; and 43 patients were treated with placebo. These patients were between the ages of 23 and 89 years (average 55 years); 173 patients were male and 39 were female; and 143 patients were White/Caucasian, 27 were Black/African American, 24 were Hispanic/Latino and 18 were all other ethnicities. Common co-morbid conditions among the enrolled patients included hypertension (72%), dyslipidemia (49%), chronic kidney disease (28%), diabetes (24%), coronary artery disease (18%), arrhythmia (16%), and cardiac failure/left ventricular dysfunction (12%).

Because clinical studies are conducted under widely varying and controlled conditions, adverse reaction rates observed in clinical studies of a drug cannot be directly compared to rates in the clinical studies of another drug, and may not predict the rates observed in a broader patient population in clinical practice.

Anaphylaxis:

Diagnostic criteria of anaphylaxis were skin or mucosal tissue involvement, and, either airway compromise, and/or reduced blood pressure with or without associated symptoms, and a temporal relationship to KXX or placebo injection with no other identifiable cause. Using these clinical criteria, anaphylaxis was identified in 14 (5.1%) of 273 total patients studied in the clinical program of IV KXX. The frequency was 6.5% for the every 2-week dosing regimen (8 of 123 patients), and 4.8% for the 4-week dosing frequency (6 of 126) of KXX. There were no cases of anaphylaxis in patients receiving placebo.

Anaphylaxis generally occurred within 2 hours after treatment. This occurred with patients being pre-treated with an oral antihistamine, intravenous corticosteroid, and acetaminophen.

Infusion Reactions:

Infusion reactions occurred in 26% of patients in the 2 week dosing regimen group and 41% of patients in the 4 week dosing regimen group, compared to 5% of placebo-treated patients.

Manifestations of these reactions included urticaria (frequency of 10.6%), dyspnea (frequency of 7.1%), chest discomfort (frequency of 9.5%), chest pain (frequency of 9.5%), erythema (frequency of 9.5%), and pruritus (frequency of 9.5%). These manifestations overlap with the symptoms of anaphylaxis, but in a given patient did not occur together to satisfy the clinical criteria for diagnosing anaphylaxis. Infusion reactions are thought to result from release of various mediators, such as cytokines. Infusion reactions occurred at any time during a course of treatment with approximately 3% occurring with the first infusion, and approximately 91% occurred during the time of infusion. Some infusion reaction manifestations were reduced with slowing the rate of infusion, or stopping the infusion and restarting the infusion at a slower rate. These infusion reactions occurred with all patients being pre-treated with an oral antihistamine, intravenous corticosteroid and acetaminophen.

Gout Flares:

Gout flares were common in the study patients before randomization to treatment, with patients experiencing an average of 10 flares in the preceding 18 months prior to study entry.

During the controlled treatment period with KXX or placebo, the frequencies of gout flares were high in all treatment groups, but more so with KXX treatment during the first 3 months of treatment, which seemed to decrease in the subsequent 3 months of treatment. The percentages of patients with any flare for the first 3 months were 74%, 81%, and 51%, for KXX 8 mg every 2 weeks, KXX 8 mg every 4 weeks, and placebo, respectively. The percentages of patients with any flare for the subsequent 3 months were 41%, 57%, and 67%, for KXX 8 mg every 2 weeks, KXX 8 mg every 4 weeks, and placebo, respectively. Patients received gout flare prophylaxis with colchicine and/or non-steroidal anti-inflammatory drugs (NSAIDs) starting at least one week before receiving KXX.

Congestive Heart Failure:

Two cases of congestive heart failure exacerbation occurred during the trials in patients receiving treatment with KXX 8 mg every 2 weeks. No cases were reported in placebo-treated patients. Four subjects had exacerbations of pre-existing congestive heart failure while receiving KXX 8 mg every 2 weeks during the open-label extension study.

Other Adverse Reactions:

The most commonly reported adverse reactions that occurred in greater than or equal to 5% of patients treated with KXX 8 mg every 2 weeks are provided in Table 4.

TABLE 4

Adverse Reactions Occurring in 5% or More of Patients Treated with KXX Compared to Placebo

| Adverse Reaction (Preferred Team) | KXX 8 mg every 2 weeks (N = 85) N$^a$ (%) | Placebo (N = 43) N (%) |
|---|---|---|
| Gout Flare | 65 (77%) | 35 (81%) |
| Infusion reaction | 22 (26%) | 2 (5%) |
| Nausea | 10 (12%) | 1 (2%) |
| Contusion$^b$ or Ecchymosis$^b$ | 9 (11%) | 2 (5%) |
| Nasopharyngitis | 6 (7%) | 1 (2%) |
| Constipation | 5 (6%) | 2 (5%) |
| Chest Pain | 5 (6%) | 1 (2%) |
| Anaphylaxis | 4 (5%) | 0 (0%) |
| Vomiting | 4 (5%) | 1 (2%) |

$^a$If the same subject in a given group had more than one occurrence in the same preferred term event category, the subject was counted only once.
$^b$Most did not occur on the day of infusion and could be related to other factors (e.g. concomitant medications relevant to contusion or ecchymosis, insulin dependent diabetes mellitus).

Example 27—Immunogenicity

Anti-pegloticase antibodies developed in 92% of patients treated with KXX every 2 weeks, and 28% for placebo. Anti-PEG antibodies were also detected in 42% of patients treated with KXX. High anti-pegloticase antibody titer was associated with a failure to maintain pegloticase-induced normalization of uric acid. The impact of anti-PEG antibodies on patients' responses to other PEG-containing therapeutics is unknown.

There was a higher incidence of infusion reactions in patients with high anti-pegloticase antibody titer: 53% (16 of 30) in the KXX every 2 weeks group compared to 6% in patients who had undetectable or low antibody titers. Using a dosage regimen as described herein, only a single infusion reaction occurred with strict adherence to the criteria set forth for stopping treatment, i.e., a serum uric acid level greater than 6 mg/dL.

As with all therapeutic proteins, there is a potential for immunogenicity. The observed incidence of antibody positivity in an assay is highly dependent on several factors including assay sensitivity and specificity and assay methodology, sample handling, timing of sample collection, concomitant medications, and underlying disease. For these reasons, the comparison of the incidence of antibodies to pegloticase with the incidence of antibodies to other products may be misleading.

Example 28—Drug Interactions

Pregnancy—Pegloticase was not teratogenic in rats and rabbits at approximately 50 and 75 times the maximum recommended human dose (MRHD), respectively (on a mg/m2 basis at maternal doses up to 40 and 30 mg/kg twice weekly, in rats and rabbits, respectively). Statistically significant decreases in mean fetal and pup body weights were observed at approximately 50 and 75 times the MRHD respectively (on a mg/m2 basis at maternal doses up to 40 and 30 mg/kg every other day, in rats and rabbits, respectively). No effects on mean fetal body weights were observed at approximately 10 and 25 times the MRHD in rats and rabbits, respectively (on a mg/m2 basis at maternal doses up to 10 mg/kg twice weekly in both species).

Geriatric Use—Of the total number of patients treated with KXX 8 mg every 2 weeks in the controlled studies, 34% (29 of 85) were 65 years of age and older and 12% (10 of 85) were 75 years of age and older. No overall differences in safety or effectiveness were observed between older and younger patients, but greater sensitivity of some older individuals cannot be ruled out. No dose adjustment is needed for patients 65 years of age and older.

Renal Impairment—No dose adjustment is required for patients with renal impairment. A total of 32% (27 of 85) of patients treated with KXX 8 mg every 2 weeks had a creatinine clearance of less than or equal to 62.5 mL/min. No overall differences in efficacy were observed.

Example 29—Overdosage

No reports of overdosage with KXX have been reported. The maximum dose that has been administered as a single intravenous dose is 12 mg as uricase protein.

Example 30—Pharmacodynamics

Approximately 24 hours following the first dose of KXX, mean plasma uric acid levels for subjects in the KXX groups were 0.7 mg/dL for the KXX 8 mg every 2 weeks group. In comparison, the mean plasma uric acid level for the placebo group was 8.2 mg/dL.

In a single-dose, dose-ranging trial, following 1-hour intravenous infusions of 0.5, 1, 2, 4, 8 or 12 mg of pegloticase in 24 patients with symptomatic gout (n=4 subjects/dose group), plasma uric acid decreased with increasing pegloticase dose or concentrations. The duration of suppression of plasma uric acid appeared to be positively associated with pegloticase dose. Sustained decrease in plasma uric acid below the solubility concentration of 6 mg/dL for more than 300 hours was observed with doses of 8 mg and 12 mg.

Example 31—Pharmacokinetics

Pegloticase levels were determined in serum based on measurements of uricase enzyme activity.

Following single intravenous infusions of 0.5 mg to 12 mg pegloticase in 23 patients with symptomatic gout, maximum serum concentrations of pegloticase increased in proportion to the dose administered. The population pharmacokinetic analysis showed that age, sex, weight, and creatinine clearance did not influence the pharmacokinetics of pegloticase. Significant covariates included in the model for determining clearance and volume of distribution were found to be body surface area and anti-pegloticase antibodies.

The pharmacokinetics of pegloticase has not been studied in children and adolescents. No formal studies were conducted to examine the effects of either renal or hepatic impairment on pegloticase pharmacokinetics.

Example 32—Nonclinical Toxicology

Carcinogenesis, Mutagenesis, Impairment of Fertility—Long-term animal studies have not been performed to evaluate the carcinogenic potential of pegloticase.

The genotoxic potential of pegloticase has not been evaluated. There was no evidence of impairment on fertility at pegloticase doses up to 40 mg/kg (approximately 50 times the MRHD on mg/m2 basis) every other day in rats.

Animal Toxicology and/or Pharmacology

Pegloticase at similar to and higher than the maximum recommended human dose (MRHD) on a plasma AUC basis [at intravenous (IV) doses of ≥0.4 mg/kg in dogs] caused cytoplasmic vacuoles in multiple organs, and edema and histiocyte infiltration in the aortic outflow tract in dogs. Organs with cytoplasmic vacuoles included the spleen, adrenal gland, liver, heart, duodenum, and jejunum. Vacuoles in the spleen, adrenal glands, and heart persisted after a 1-year recovery period at pegloticase dose (≥1.5 mg/kg in dogs) approximately 5 times the MRHD, but were absent at a dose similar to the MRHD. Vacuoles in the liver, duodenum, and jejunum persisted after a 3-month recovery period at a pegloticase dose (10 mg/kg in dogs) approximately 30 times the MRHD, but were absent at doses less than or equal to 1.5 mg/kg approximately 5 times and similar to the MRHD. The edema and histiocyte infiltration in the aortic outflow tract was absent after recovery periods of 6 and 12 months, respectively.

Vacuoles in the spleen, liver, duodenum, and jejunum were within macrophages and most likely represented phagocytic removal of pegloticase from the circulation. However, the vacuolated cells in the heart and adrenal gland did not stain as macrophages. In the aortic outflow tract of the heart, vacuoles were in the cytoplasm of endothelial cells in the intimal lining of the aorta. In the adrenal gland, vacuoles were located within cortical cells in the *Zona reticularis* and *Zona fasciculata*. The clinical significance of these findings and the functional consequences are unknown.

Example 33—Clinical Studies

The efficacy of KXX was studied in adult patients with chronic gout refractory to conventional therapy in two replicate, multicenter, randomized, double-blind, placebo controlled studies of six months duration: Trial 1 and Trial 2. Patients were randomized to receive KXX 8 mg every 2 weeks or every 4 weeks or placebo in a 2:2:1 ratio.

Studies were stratified for the presence of tophi. Seventy-one percent (71%) of patients had baseline tophi. All patients were prophylaxed with an oral antihistamine, intravenous corticosteroid and acetaminophen. Patients also received prophylaxis for gout flares with non-steroidal anti-inflammatory drugs (NSAIDs) or colchicine, or both, beginning at least one week before KXX treatment unless medically contraindicated or not tolerated. Patients who completed the randomized clinical trials were eligible to enroll in a 2-year open label extension study.

Entry criteria for patients to be eligible for the trials were: baseline serum uric acid (SUA) of at least 8 mg/dL; had symptomatic gout with at least 3 gout flares in the previous 18 months or at least 1 gout tophus or gouty arthritis; and had a self-reported medical contraindication to allopurinol or medical history of failure to normalize uric acid (to less than 6 mg/dL) with at least 3 months of allopurinol treatment at the maximum medically appropriate dose.

The mean age of study subjects was 55 years (23-89); 82% were male, mean body mass index (BMI) was 33 kg/m2, mean duration of gout was 15 years, and mean baseline SUA was 10 mg/dL.

To assess the efficacy of KXX in lowering uric acid, the primary endpoint in both trials was the proportion of patients who achieved plasma uric acid (PUA) less than 6 mg/dL for at least 80% of the time during Month 3 and Month 6. As shown in Table 5, a greater proportion of patients treated with KXX every 2 weeks achieved urate lowering to below 6 mg/dL than patients receiving placebo. Although the 4 week regimen also demonstrated efficacy for the primary endpoint, this regimen was associated with increased frequency of anaphylaxis and infusion reactions and less efficacy with respect to tophi.

TABLE 5

Plasma Uric Acid <6 mg/dL for at Least 80% of the Time During Months 3 and 6

| Treatment Group | N | Number (%) of Subjects Who Met Response Criteria | 95% Confidence Interval[1] | P-Value[2] |
|---|---|---|---|---|
| Trial 1 | | | | |
| Pegloticase 8 mg every 2 weeks | 43 | 20 (47%) | [32%, 61%] | <0.001 |
| Pegloticase 8 mg every 4 weeks | 41 | 8 (20%) | [7%, 32%] | 0.044 |
| Placebo | 20 | 0 (0%) | | |
| Trial 2 | | | | |
| Pegloticase 8 mg every 2 weeks | 42 | 16 (38%) | [23%, 53%] | <0.001 |
| Pegloticase 8 mg every 4 weeks | 43 | 21 (49%) | [34%, 64%] | <0.001 |
| Placebo | 23 | 0 (0%) | | |

[1]95% confidence interval for differences in responder rate between pegloticase group vs. placebo.
[2]P-value using Fisher's exact test to compare pegloticase group vs. placebo Based on post-hoc analyses of the clinical trial data, if KXX had been stopped when a patient's uric acid level rose to greater than 6 mg/dL on a single occasion, the incidence of infusion reactions would have been reduced by approximately 67%, but the success rates for the primary efficacy endpoint would have been reduced by approximately 20%. If KXX had been stopped after 2 consecutive uric acid levels greater than 6 mg/dL, the incidence of infusion reactions would have been half, and there would have been little change in the efficacy outcome.

The effect of treatment on tophi was a secondary efficacy endpoint and was assessed using standardized digital photography, image analysis, and a Central Reader blinded to treatment assignment. Approximately 70% of patients had tophi at baseline. A pooled analysis of data from Trial 1 and Trial 2 was performed as pre-specified in the protocols. At Month 6, the percentage of patients who achieved a complete response (defined as 100% resolution of at least one target tophus, no new tophi appear and no single tophus showing progression) was 45%, 26%, and 8%, with KXX 8 mg every 2 weeks, KXX 8 mg every 4 weeks, and placebo, respectively. The difference between KXX and placebo was statistically significant for the every-2-week dosing regimen, but not for the every-4-week dosing regimen.

What is claimed is:

1. A method of treating gout in a patient, the method comprising administering a PEGylated uricase and azathioprine (AZA) to the patient; wherein the PEGylated uricase is administered weekly for a total of 3 weeks at a dose of 8 mg protein and then administered bi-weekly at a dose of 8 mg protein, wherein the AZA is dosed at about 1.25-5.5 mg/kg daily.

2. The method of claim 1, further comprising administering prednisone.

3. The method of claim 1, wherein the AZA is administered orally.

4. The method of claim 3, wherein the AZA dose is about 1.25 mg/kg daily for one week followed by about 2.5 mg/kg daily.

5. The method of claim 1, wherein AZA administration is initiated 2 weeks prior to the first PEGylated uricase dose.

6. The method of claim 1, wherein the patient has a serum uric acid level of >6 mg/dL before beginning treatment.

7. The method of claim 1, wherein the patient has a co-morbid condition selected from the group consisting of hypertension, dyslipidemia, chronic kidney disease, diabetes, coronary artery disease, arrhythmia, and cardiac failure.

8. The method of claim 1, comprising measuring a level of one or more of trough PEGylated uricases, anti-PEGylated uricase antibodies, and anti-monomethyoxypoly(ethylene glycol) (PEG) antibodies.

9. The method of claim 1, wherein the administration of the PEGylated uricase is effective in reducing a tophus burden in the patient.

10. The method of claim 9, wherein:
 (a) at least 1 tophus is completely resolved as determined by comparison of photography of a tophus before and after administration of the PEGylated uricase;
 (b) no new tophi appear after the administration of the PEGylated uricase; and
 (c) no single tophus shows progression after the administration of the PEGylated uricase.

11. The method of claim 1, wherein the serum uric acid level is reduced to less than, or equal to, 6 mg/dL.

12. A method of treating gout in a patient weighing less than 120 kg, comprising administering a PEGylated uricase and azathioprine (AZA) to the patient, wherein the treatment comprises a tolerizing dose regimen, wherein, during the tolerizing dose regimen, the PEGylated uricase is administered weekly for 3 weeks at a dose of 8 mg protein, and the AZA is administered on a daily basis at about 1.25-5.5 mg/kg starting 2 weeks prior to the first PEGylated uricase dose; and, after the tolerizing dose regimen, the PEGylated uricase is administered every 2 weeks at a dose of 8 mg protein, and the AZA is administered on a daily basis at about 1.25-5.5 mg/kg.

13. The method of claim 12 wherein the AZA dose is about 1.25 mg/kg.

14. A method of treating gout in a patient weighing ≥120 kg, comprising administering a PEGylated uricase and azathioprine (AZA) to the patient, wherein the treatment comprises a tolerizing dose regimen; wherein, during the tolerizing dose regimen, the PEGylated uricase is administered weekly for 3 weeks at a dose of 8 mg protein, 12 mg protein, or 16 mg protein, and the AZA is administered on a daily basis at about 1.25-5.5 mg/kg starting 2 weeks prior to the first PEGylated uricase dose; and, after the tolerizing dose regimen, the PEGylated uricase is administered every 2 weeks at a dose of 8 mg protein, and the AZA is administered on a daily basis at about 1.25-5.5 mg/kg.

15. The method of claim 14 wherein the AZA dose is about 1.25 mg/kg.

16. The method of claim 14 wherein, during the tolerizing dose regimen, the PEGylated uricase is administered weekly for 3 weeks at a dose of 8 mg.

* * * * *